United States Patent
Kawashima

(10) Patent No.: US 9,655,593 B2
(45) Date of Patent: May 23, 2017

(54) MEDICAL DIAGNOSTIC APPARATUS, METHOD FOR OPERATING MEDICAL DIAGNOSTIC APPARATUS, AND COMPUTER-READABLE RECORDING MEDIUM

(71) Applicant: OLYMPUS CORPORATION, Tokyo (JP)

(72) Inventor: Tomonao Kawashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/180,569

(22) Filed: Jun. 13, 2016

(65) Prior Publication Data
US 2016/0278743 A1 Sep. 29, 2016

Related U.S. Application Data

(63) Continuation of application No. PCT/JP2015/062606, filed on Apr. 24, 2015.

(30) Foreign Application Priority Data

Jun. 11, 2014 (JP) ................. 2014-121002

(51) Int. Cl.
*A61B 5/00* (2006.01)
*A61B 8/08* (2006.01)
(Continued)

(52) U.S. Cl.
CPC ............ *A61B 8/5207* (2013.01); *A61B 8/085* (2013.01); *A61B 8/14* (2013.01); *A61B 8/4444* (2013.01);
(Continued)

(58) Field of Classification Search
CPC ....... A61B 5/0095; A61B 5/4848; A61B 5/00; A61B 8/485; A61B 8/02; A61B 8/5207
See application file for complete search history.

(56) References Cited

U.S. PATENT DOCUMENTS

2004/0209237 A1* 10/2004 Flewelling ........... A61B 5/0059
435/4
2011/0257527 A1* 10/2011 Suri ..................... A61B 8/0858
600/440

(Continued)

FOREIGN PATENT DOCUMENTS

JP H09-084793 A 3/1997
JP 5079177 B2 11/2012
(Continued)

OTHER PUBLICATIONS

International Search Report dated Jul. 7, 2015 issued in PCT/JP2015/062606.
(Continued)

*Primary Examiner* — Joel Lamprecht
(74) *Attorney, Agent, or Firm* — Scully, Scott, Murphy & Presser, P.C.

(57) ABSTRACT

A medical diagnostic apparatus includes: a feature calculating unit configured to calculate a plurality of kinds of features that is based on luminance information or frequency spectrum information obtained from a received signal from a specimen, and that relates to attributes of a tissue of the specimen; a classification unit configured to: classify the attributes of the tissue of the specimen by using a feature determined among the plurality of kinds of features calculated by the feature calculating unit according to a classification item selected in advance from a plurality of classification items assigned for each classification purpose; and assign visual information according to a classification result to pixels of an image based on the received signal; and a (Continued)

feature image data generating unit configured to generate feature image data on which the visual information assigned to the pixels of the image based on the received signal is superimposed.

14 Claims, 18 Drawing Sheets

(51) Int. Cl.
    *A61B 8/14*         (2006.01)
    *A61B 8/00*         (2006.01)
    *G01S 7/52*         (2006.01)
    *G06T 7/00*         (2017.01)

(52) U.S. Cl.
    CPC ........ *A61B 8/5223* (2013.01); *G01S 7/52033* (2013.01); *G01S 7/52036* (2013.01); *G01S 7/52071* (2013.01); *G06T 7/0012* (2013.01); *A61B 8/461* (2013.01); *A61B 8/467* (2013.01); *G06T 2207/10132* (2013.01); *G06T 2207/20081* (2013.01); *G06T 2207/30096* (2013.01)

(56) References Cited

U.S. PATENT DOCUMENTS

2012/0136255 A1    5/2012    Fan et al.
2013/0012818 A1    1/2013    Miyaki

FOREIGN PATENT DOCUMENTS

WO    WO 2011/155168 A1    12/2011
WO    WO 2012/011414 A1    1/2012

OTHER PUBLICATIONS

Japanese Office Action dated Oct. 13, 2015 issued in JP 2015-540935.

Japanese Office Action dated Feb. 9, 2016 issued in JP 2015-540935.

\* cited by examiner

FIG.7

| No | CLASSIFICATION ITEM | CLASSIFICATION ATTRIBUTE | FEATURE | COLOR | RANGE |
|---|---|---|---|---|---|
| I | TUMOR SCREENING | NORMAL TISSUE/ MALIGNANT TUMOR TISSUE | Sd. M | RED | $0 \leq Sd.\ M < M_{11}$ |
| | | | | PINK | $M_{11} \leq Sd.\ M < M_{12}$ |
| | | | | MASK | $Sd.\ M \geq M_{12}$ |
| II | MALIGNANCY/ BENIGNANCY DISTINCTION | MALIGNANT TUMOR TISSUE/BENIGN TUMOR TISSUE | Mean M | MASK | $0 \leq Mean\ M < M_{21}$ |
| | | | | BLUE | $M_{21} \leq Mean\ M < M_{22}$ |
| | | | | WATER COLOR | $M_{22} \leq Mean\ M < M_{23}$ |
| | | | | YELLOW | $M_{23} \leq Mean\ M < M_{24}$ |
| | | | | PINK | $M_{24} \leq Mean\ M < M_{25}$ |
| | | | | RED | $Mean\ M \geq M_{25}$ |
| III | FOLLOW-UP DETERMINATION 1 | FOLLOW-UP-REQUIRED TISSUE/ BENIGN TUMOR TISSUE | Sd. I | RED | $0 \leq Sd.\ I < I_1$ |
| | | | | PINK | $I_1 \leq Sd.\ I < I_2$ |
| | | | | WATER COLOR | $I_2 \leq Sd.\ I < I_3$ |
| | | | | BLUE | $I_3 \leq Sd.\ I < I_4$ |
| | | | | MASK | $Sd.\ I \geq I_4$ |
| IV | FOLLOW-UP DETERMINATION 2 | FOLLOW-UP-REQUIRED TISSUE/ MALIGNANT TUMOR TISSUE | d(Mean M, Sd. I) | RED | $0 \leq D < d_1$ |
| | | | | PINK | $d_1 \leq D < d_2$ |
| | | | | GREEN | $d_2 \leq D < d_3$ |
| | | | | YELLOW | $d_3 \leq D < d_4$ |
| | | | | MASK | $d \geq d_4$ |
| ... | ... | ... | ... | ... | ... |

| No | CLASSIFICATION ITEM | CLASSIFICATION ATTRIBUTE |
|---|---|---|
| I | TUMOR SCREENING | NORMAL TISSUE/MALIGNANT TUMOR TISSUE |
| II | MALIGNANCY/BENIGNANCY DISTINCTION | MALIGNANT TUMOR TISSUE/BENIGN TUMOR TISSUE |
| III | FOLLOW-UP DETERMINATION 1 | FOLLOW-UP-REQUIRED TISSUE/BENIGN TUMOR TISSUE |
| IV | FOLLOW-UP DETERMINATION 2 | FOLLOW-UP-REQUIRED TISSUE/MALIGNANT TUMOR TISSUE |
| ⋮ | ⋮ | ⋮ |

MEDICAL DIAGNOSTIC APPARATUS, METHOD FOR OPERATING MEDICAL DIAGNOSTIC APPARATUS, AND COMPUTER-READABLE RECORDING MEDIUM

CROSS REFERENCES TO RELATED APPLICATIONS

This application is a continuation of PCT international application Ser. No. PCT/JP2015/062606, filed on Apr. 24, 2015 which designates the United States, incorporated herein by reference, and which claims the benefit of priority from Japanese Patent Application No. 2014-121002, filed on Jun. 11, 2014, incorporated herein by reference.

BACKGROUND

1. Technical Field

The disclosure relates to a medical diagnostic apparatus for generating diagnostic image data by using a received signal from a specimen, a method for operating the medical diagnostic apparatus, and a computer-readable recording medium.

2. Related Art

Conventionally, as a medical diagnostic apparatus for generating image data used for a diagnosis by using a received signal from a specimen, a technology for setting a plurality of learning windows from an image, plotting texture features of learning windows set in different texture areas on a feature space, and setting a criterion for calculating the degree of similarity by using a distribution of the texture features on the feature space has been disclosed (for example, see Japanese Patent Application Laid-open Publication No. 9-84793). According to the technology, all the tissues of a specimen can be automatically discriminated from each other, and, for example, the surface of a luminal organ and a boundary of a tissue such as a tumor can be detected using a simple method.

More specifically, for example, a case will be considered in which a tissue under examination is automatically determined to be one of a tissue A, a tissue B, a tissue C, and a lumen. According to this technology, first, two kinds among the four kinds of tissues are selected. Next, as pathological results, features of known specimens of the two kinds and a feature of the tissue of an unknown specimen under examination are compared with each other. Next, one of the features of the known tissues of the two kinds to which the feature of the tissue under examination is closer is determined. In this way, the determination is repeated while the selection of a combination of tissues of two kinds is changed. Then, by determining the tissue under examination to be a tissue determined to have a highest frequency based on a plurality of determination results of the tissues of the two kinds, the unknown tissues are classified.

SUMMARY

In some embodiments, a medical diagnostic apparatus includes: a feature calculating unit configured to calculate a plurality of kinds of features that is based on luminance information or frequency spectrum information obtained from a received signal from a specimen, and that relates to attributes of a tissue of the specimen; a classification unit configured to: classify the attributes of the tissue of the specimen by using a feature determined among the plurality of kinds of features calculated by the feature calculating unit according to a classification item selected in advance from a plurality of classification items assigned for each classification purpose; and assign visual information according to a classification result to pixels of an image based on the received signal; and a feature image data generating unit configured to generate feature image data on which the visual information assigned to the pixels of the image based on the received signal is superimposed.

In some embodiments, a method for operating a medical diagnostic apparatus that generates diagnostic image data based on a received signal from a specimen is provided. The method includes: calculating, by a feature calculating unit, a plurality of kinds of features in luminance information or frequency spectrum information obtained from the received signal; by a classification unit, classifying attributes of a tissue of the specimen by using a feature determined among the plurality of kinds of features according to a classification item selected in advance from a plurality of classification items assigned for each classification purpose, and assigning visual information according to a classification result to pixels of an image based on the received signal; and generating, by a feature image data generating unit, feature image data on which the visual information assigned to the pixels of the image based on the received signal is superimposed.

In some embodiments, a non-transitory computer-readable recording medium with an executable program stored thereon is provided. The program instructs a medical diagnostic apparatus that generates diagnostic image data based on a received signal from a specimen, to execute: calculating, by a feature calculating unit, a plurality of kinds of features in luminance information or frequency spectrum information obtained from the received signal; by a classification unit, classifying attributes of a tissue of the specimen by using a feature determined among the plurality of kinds of features according to a classification item selected in advance from a plurality of classification items assigned for each classification purpose, and assigning visual information according to a classification result to pixels of an image based on the received signal; and generating, by a feature image data generating unit, feature image data on which the visual information assigned to the pixels of the image based on the received signal is superimposed.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a diagram that schematically illustrates classification information stored by a classification information storage unit according to the first embodiment of the present invention;

FIG. 13 is a diagram that illustrates an example of the display of a selection screen displayed by a display unit when an input unit receives a selection input of a classification item;

DETAILED DESCRIPTION

Hereinafter, modes for carrying out the present invention (hereinafter, referred to as "embodiment(s)") will be described with reference to the accompanying drawings.

First Embodiment

Figure 1:
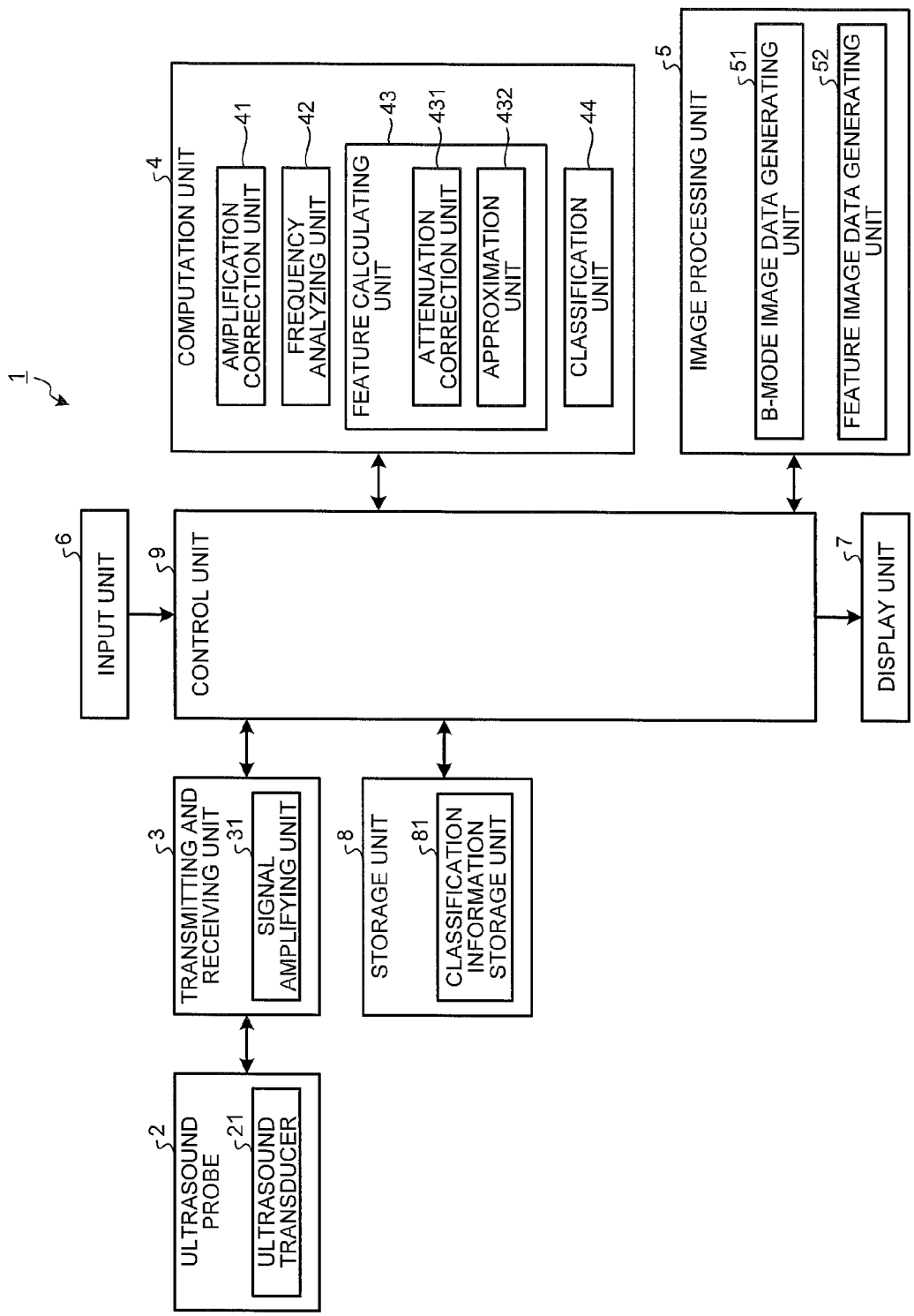
FIG. 1 is a block diagram that illustrates the configuration of an ultrasound observation apparatus that is a medical diagnostic apparatus according to a first embodiment of the present invention.

FIG. 1 is a block diagram that illustrates the configuration of an ultrasound observation apparatus that is a medical diagnostic apparatus according to a first embodiment of the present invention. An ultrasound observation apparatus 1 illustrated in FIG. 1 is an apparatus used for observing a specimen as a diagnosis target by using ultrasound waves.

The ultrasound observation apparatus 1 includes: an ultrasound probe 2 that outputs an ultrasound pulse to the outside and receives an ultrasound echo reflected on the outside; a transmitting and receiving unit 3 that transmits and receives electric signals to and from the ultrasound probe 2; a computation unit 4 that performs predetermined calculation on an electric echo signal acquired by converting a ultrasound echo into an electric signal; an image processing unit 5 that generates image data corresponding to an electric echo signal; an input unit 6 that is realized by a user interface such as a keyboard, a mouse, or a touch panel and receives input of various kinds of information; a display unit 7 that is realized by using a display panel configured by a liquid crystal, an organic electro luminescence (EL), or the like and displays various kinds of information including an image generated by the image processing unit 5; a storage unit 8 that stores various kinds of information necessary for the observation of an ultrasound wave; and a control unit 9 that controls the operation of the ultrasound observation apparatus 1.

The ultrasound observation apparatus 1 is configured by: the ultrasound probe 2 in which an ultrasound transducer 21 is disposed; and a processing device (processor), to which the ultrasound probe 2 is detachably connected, having the above-described parts other than the ultrasound probe 2 disposed therein. Here, the ultrasound probe 2 may be one of: an external probe that emits ultrasound waves from the surface of a living body; a miniature ultrasound probe that includes an elongate insertion part configured to be inserted into a lumen such as an alimentary tract, a biliopancreatic duct, or a blood vessel; and an ultrasound endoscope including an optical system in addition to an intraluminal ultrasound probe. Among these, if the intraluminal ultrasound probe is employed such as the ultrasound endoscope, an ultrasound transducer 21 is disposed on the distal end side of the insertion part of the intraluminal ultrasound probe, and the intraluminal ultrasound probe is detachably connected to a processing device on the proximal end side.

The ultrasound probe 2 includes the ultrasound transducer 21 that converts an electric pulse signal received from the transmitting and receiving unit 3 into an ultrasonic pulse (acoustic pulse) and converts an ultrasound echo reflected on an external specimen into an electric echo signal. The ultrasound probe 2 may cause the ultrasound transducer 21 to mechanically scan or may cause the ultrasound transducer 21 to electronically scan by arranging a plurality of elements in an array pattern as the ultrasound transducer 21 and electronically switching elements relating to transmission/reception or applying a delay to the transmission/reception of each element. In the first embodiment, one of a plurality of different types of ultrasound probes may be selected and used as the ultrasound probe 2.

The transmitting and receiving unit 3 is electrically connected to the ultrasound probe 2, transmits an electric pulse signal to the ultrasound probe 2, and receives an echo signal that is an electric signal received from the ultrasound probe 2. More specifically, the transmitting and receiving unit 3 generates an electric pulse signal based on a waveform and transmission timing set in advance and transmits the generated pulse signal to the ultrasound probe 2.

Figure 2:
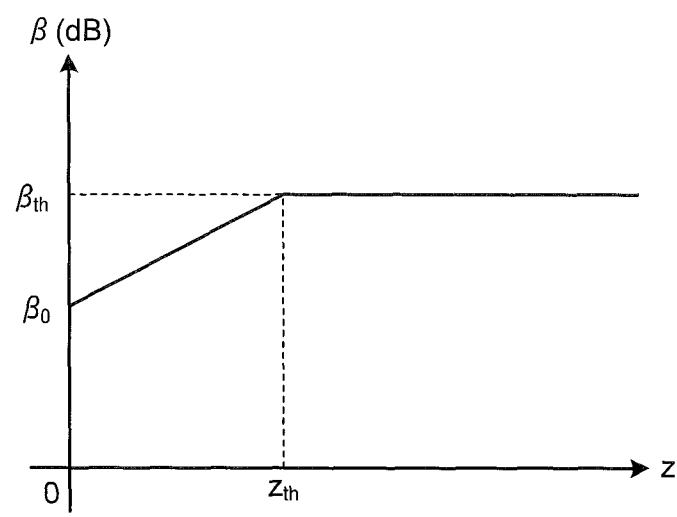
FIG. 2 is a diagram that illustrates a relation between a reception depth and an amplification factor in an amplification process performed by a signal amplifying unit of the ultrasound observation apparatus according to the first embodiment of the present invention.

The transmitting and receiving unit 3 includes a signal amplifying unit 31 that amplifies an echo signal. More specifically, the signal amplifying unit 31 performs a sensitivity time control (STC) correction in which an echo signal is amplified using a higher amplification factor as the reception depth of the echo signal is larger. FIG. 2 is a diagram that illustrates a relation between a reception depth and an amplification factor in an amplification process performed by the signal amplifying unit 31. A reception depth z illustrated in FIG. 2 is an amount calculated based on an elapsed time from a reception start time point of an ultrasound wave. As illustrated in FIG. 2, in a case where the reception depth z is less than a threshold $z_{th}$, the amplification factor β (dB) linearly increases from $β_0$ to $β_{th}$ ($>β_0$) in accordance with an increase in the reception depth z. On the other hand, in a case where the reception depth z is the threshold $z_{th}$ or more, the amplification factor β (dB) takes a constant value $β_{th}$. The value of the threshold $z_{th}$ is a value at which an ultrasound wave signal received from a specimen is almost attenuated, and the noise is dominant. More generally, the amplification factor β may be configured to monotonously increase in accordance with an increase in the reception depth z in a case where the reception depth z is less than the threshold $z_{th}$.

The transmitting and receiving unit 3 generates a digital RF signal of the time domain by performing an A/D conversion, after performing a process of filtering and the like for an echo signal amplified by the signal amplifying unit 31 and outputs the generated digital RF signal. In addition, in a case where the ultrasound probe 2 causes the ultrasound transducer 21, in which a plurality of elements are arranged in an array pattern, to electronically scan, the transmitting and receiving unit 3 includes a multi-channel circuit used for beam composition corresponding to the plurality of elements.

The computation unit 4 includes: an amplification correction unit 41 that performs an amplification correction on a digital radio frequency (RF) signal output by the transmitting and receiving unit 3 such that the amplification factor β becomes constant without being dependent on the reception depth; a frequency analyzing unit 42 that calculates a frequency spectrum by performing a frequency analysis by executing Fast Fourier Transform (FFT) for the digital RF signal for which the amplification correction has been performed; a feature calculating unit 43 that calculates a plurality of kinds of features of the frequency spectrum; and a classification unit 44 that classifies the attribute of a tissue of a specimen by using a feature corresponding to a classification item of a tissue to be diagnosed that has been selected in advance. The computation unit 4 is realized by a central processing unit (CPU), various calculation circuits, and the like.

Figure 3:
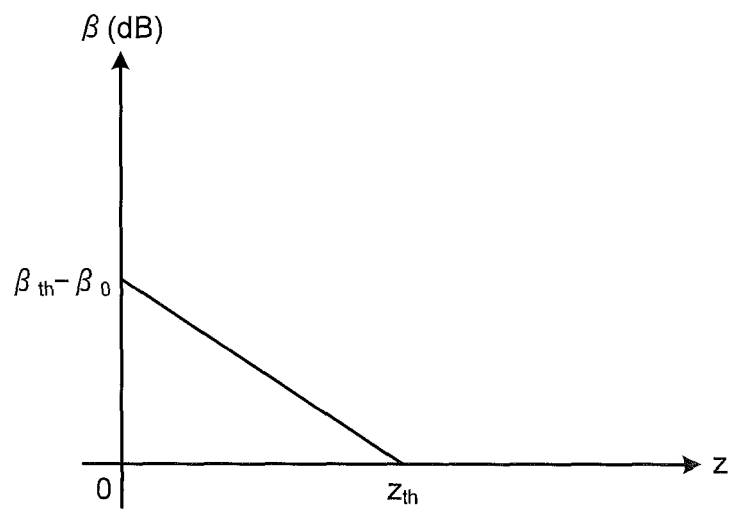
FIG. 3 is a diagram that illustrates a relation between a reception depth and an amplification factor in an amplification process performed by an amplification correction unit of the ultrasound observation apparatus according to the first embodiment of the present invention.

FIG. 3 is a diagram that illustrates a relation between the reception depth and the amplification factor in an amplification process performed by the amplification correction unit 41. As illustrated in FIG. 3, the amplification factor β (dB) used in the amplification process performed by the amplification correction unit 41 takes a maximum value of "$β_{th}-β_0$" when the reception depth z is zero, linearly decreases from when the reception depth z is zero until the reception depth arrives at the threshold $z_{th}$, and is zero when the reception depth z is the threshold $z_{th}$ or more. As the amplification correction unit 41 amplifies and corrects the digital RF signal by using the amplification factor set in this way, the influence of an STC correction in the signal amplifying unit 31 is offset, and a signal having a constant amplification factor $β_{th}$ can be output. It is apparent that the relation between the reception depth z and the amplification factor β in the amplification correction unit 41 is different in accordance with the relation between the reception depth and the amplification factor in the signal amplifying unit 31.

The reason for performing such an amplification correction will be described. The STC correction is a correction process for excluding the influence of attenuation from the amplitude of an analog signal waveform by amplifying the amplitude of the analog signal waveform to be uniform over all the frequency bands using an amplification factor monotonously increasing with respect to the depth. For this reason, in a case where a B-mode image using the amplitude of an echo signal is generated and in a case where an even tissue is scanned, by performing the STC correction, the luminance value becomes constant regardless of the depth. In other words, an effect of excluding the influence of attenuation from a B-mode luminance value can be acquired. On the other hand, as in the first embodiment, in a case where a result of an analysis acquired by calculating the frequency spectrum of an ultrasound wave is used, the influence of the attenuation associated with the propagation of the ultrasound wave cannot be accurately eliminated even when the STC correction is performed. The reason for this is that, as in Equation (1) to be described later, while the attenuation amount is different according to the frequency, the amplification factor of the STC correction is changed according to the distance and is constant without any change with respect to the frequency. A method for excluding the influence of the attenuation including the dependency of the attenuation amount on the frequency will be described later with reference to FIG. 6 and Step S9 of FIG. 12 as an "attenuation correction process".

In order to solve the situation described above (i.e., the situation where influence of attenuation associated with propagation of an ultrasound wave is not accurately eliminated even when the STC correction is performed when using a result of the analysis acquired by calculating the frequency spectrum of the ultrasound wave), a received signal on which the STC correction is performed may be output when generating a B-mode image whereas, when generating an image based on the frequency spectrum, new transmission other than transmission for generating the B-mode image is performed, and a received signal on which the STC correction is not performed may be output. However, in such a case, a frame rate of image data generated based on the received signal may be lowered.

Thus, in the first embodiment, in order to exclude the influence of an STC correction on a signal for which the STC correction is performed for a B-mode image while maintaining the frame rate of generated image data, the amplification factor is corrected by the amplification correction unit 41.

The frequency analyzing unit 42 calculates the frequency spectrum at a plurality of locations (data positions) on a sound ray by performing Fast Fourier Transform of an amplitude data group acquired by sampling each sound ray (line data) of a signal acquired by amplifying and correcting a digital RF signal based on an echo signal at a predetermined time interval.

Figure 4:
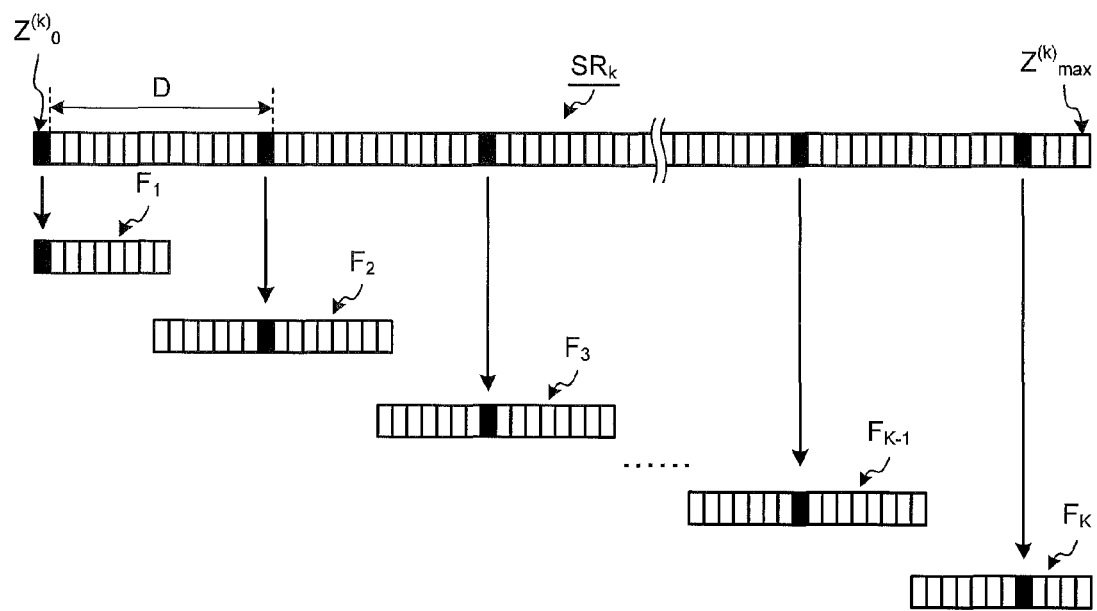
FIG. 4 is a diagram that schematically illustrates a data array in one sound ray of an ultrasonic signal.

FIG. 4 is a diagram that schematically illustrates a data array in one sound ray of an ultrasonic signal. In sound ray data $SR_k$ illustrated in FIG. 4, a white or black rectangle represents one piece of data. The sound ray data $SR_k$ is formed to be discrete at the interval of a time corresponding to a sampling frequency (for example, 50 MHz) used in the A/D conversion performed by the transmitting and receiving unit 3. Although in FIG. 4, the first data position of the sound ray data $SR_k$ of a number k (to be described later) is set as an initial value $Z^{(k)}_0$ in the direction of the reception depth z, the position of the initial value may be arbitrarily set. A result of the calculation performed by the frequency analyzing unit 42 is acquired as a complex number and is stored in the storage unit 8.

A data group $F_j$ (here, j=1, 2, ..., K) illustrated in FIG. 4 is an amplitude data group that is a target for Fast Fourier Transform. Generally, in order to perform Fast Fourier Transform, the amplitude data group needs to have data of a number of exponent of two. In this meaning, the amplitude data group $F_j$ (here, j=2, ..., K−1) has the number of data as 16 (=$2^4$) and thus is a normal data group, and the amplitude data groups $F_1$ and $F_K$ respectively have the numbers of data as 9 and 12 and are abnormal data groups. In order to perform Fast Fourier Transform on an abnormal data group, a process of generating a normal amplitude data group by inserting zero data corresponding to a shortage is performed. This point will be described in detail when explaining the process performed by the frequency analyzing unit 42, which will be described later (see FIG. 14).

Figure 5:
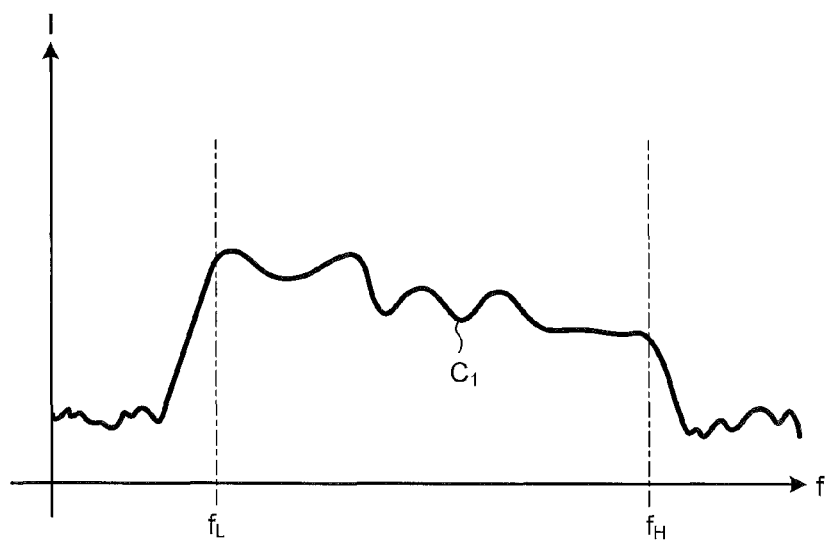
FIG. 5 is a diagram that illustrates an example of a frequency spectrum calculated by a frequency analyzing unit of the ultrasound observation apparatus according to the first embodiment of the present invention.

FIG. 5 is a diagram that illustrates an example of a frequency spectrum calculated by the frequency analyzing unit 42. More specifically, the "frequency spectrum" illustrated in FIG. 5 as an example represents "a frequency distribution of the intensity at a certain reception depth z" acquired by performing Fast Fourier Transform (FFT operation) of an amplitude data group. The "intensity" described here, for example, represents one of a parameter such as a voltage of an echo signal, power of an echo signal, sound pressure of an ultrasound wave echo, or sound energy of an ultrasound wave echo, amplitude or a time-integrated value of such a parameter, and a combination thereof. In FIG. 5, the frequency f is taken on the horizontal axis, and a decibel expression $\log_{10}(I/I_c)$ of the intensity acquired by dividing the intensity I by a specific reference intensity $I_c$ (constant) and further taking a common logarithm thereof is taken on the vertical axis. In FIG. 5 and subsequent diagrams, for the simplification of description, hereinafter, the intensity represented in a decibel expression will be simply referred to as "I". In the example illustrated in FIG. 5, the reception depth z is constant. In the first embodiment, a curve and a straight line are formed by sets of discrete points.

In the frequency spectrum $C_1$ illustrated in FIG. 5, a lower limit frequency $f_L$ and an upper limit frequency $f_H$ of a frequency band used in calculation performed hereinafter are parameters determined based on the frequency band of the ultrasound transducer 21, the frequency band of a pulse signal transmitted by the transmitting and receiving unit 3, and the like and, for example, are respectively $f_L$=3 MHz and $f_H$=10 MHz. Hereinafter, a frequency band determined based on the lower limit frequency $f_L$ and the upper limit frequency $f_H$ will be referred to as a "frequency band F".

Generally, a frequency spectrum represents a tendency that is different according to the attribute of a tissue scanned by an ultrasound wave. The reason for this is that the frequency spectrum has a correlation with the size, the number density, the acoustic impedance, and the like of a scatterer scattering the ultrasound wave. In the first embodiment, the "attribute", for example, is a malignant tumor tissue, a benign tumor tissue, an endocrine tumor tissue, a mucinous tumor tissue, a normal tissue, a vessel, or the like.

The feature calculating unit 43 includes: an attenuation correction unit 431 that performs an attenuation correcting process for correcting the influence of the attenuation of an ultrasound wave depending on the reception depth and the frequency of the ultrasound wave; and an approximation unit 432 that calculates an approximate equation of the frequency spectrum after the attenuation correction through a regression analysis.

Figure 6:
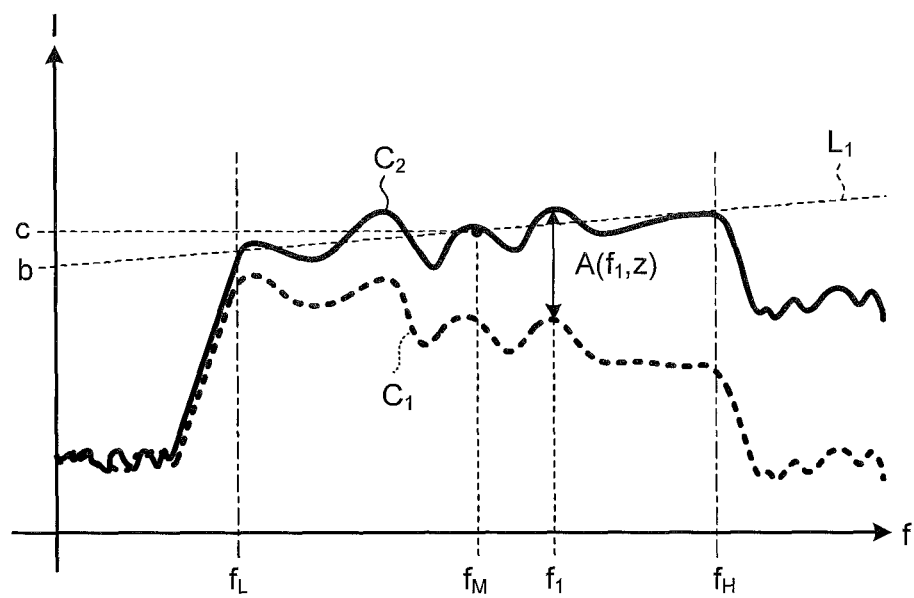
FIG. 6 is a diagram that schematically illustrates an overview of a process performed by a feature calculating unit of the ultrasound observation apparatus according to the first embodiment of the present invention.

FIG. 6 is a diagram that schematically illustrates an overview of a process performed by the feature calculating unit 43. In FIG. 6, a case will be described as an example in which the feature of the frequency spectrum $C_1$ illustrated in FIG. 5 is calculated. First, the attenuation correction unit 431 performs a correction (I(f, z)→I(f, z)+A(f, z)) of adding an attenuation amount A(f, z) represented in Equation (1) to the intensity I(f, z) at all the frequencies f for the frequency spectrum $C_1$. The attenuation amount A(f, z) of this ultrasound wave is attenuation generated while the ultrasound wave reciprocates between a reception depth of "0" and a reception depth of z and is defined as a intensity change (a difference in the decibel expression) between before and after the reciprocation. It is empirically known that this attenuation amount A(f, z) is proportional to the frequency inside a uniform tissue and is represented using Equation (1) by using a proportional coefficient as α.

$$A(f,z)=2\alpha z f \quad (1)$$

Here, α is called an attenuation rate. In addition, z is the reception depth of an ultrasound wave, and f is a frequency.

In a case where an observation target is a living body, a specific value of the attenuation rate α is 0.0 to 1.0 (dB/cm/MHz) and is more preferably 0.3 to 0.7 (dB/cm/MHz) and is determined according to a region of the living body. For example, in a case where the observation target is the pancreas, there is a case where the attenuation rate is set such that α=0.6 (dB/cm/MHz). In addition, in the first embodiment, it may be configured such that the value of the attenuation rate α is set or changeable according to an input from the input unit 6.

A frequency spectrum $C_2$ illustrated in FIG. 6 is a new frequency spectrum acquired as a result of a correction of the influence of attenuation associated with the propagation of an ultrasound wave through the attenuation correcting process.

The approximation unit 432 approximates the frequency spectrum $C_2$ by a linear expression (regression line) by performing a regression analysis at the frequency band F of the frequency spectrum $C_2$, thereby extracting parameters that are necessary for the calculation of a feature. The parameters extracted in this case are a slope a and an intercept b of a regression line $L_1$ illustrated in FIG. 6 and a mid-band fit c=$af_M$+b that is a value on the regression line at the center frequency $f_M$=($f_L$+$f_H$)/2 of the frequency band F.

Among the three features, the slope a has a correlation with the size of the scatterer of an ultrasound wave. Generally, as the size of the scatterer increases, the slope is considered to have a smaller value. In addition, the intercept b has a correlation with the size of the scatterer, a difference in the acoustic impedance, the number density (concentration) of the scatterer, and the like. More specifically, the intercept b is considered to have a larger value as the size of the scatterer is increased, to have a larger value as the difference in the acoustic impedance is increased, and to have a larger value as the number density (concentration) of the scatterer is increased. The mid-band fit c is an indirect parameter derived from the slope a and the intercept b and represents the intensity of the spectrum at the center within an effective frequency band. For this reason, the mid-band fit c is considered to have a correlation of some degree with the luminance of a B-mode image in addition to the size of the scatterer, a difference in the acoustic impedance, and the number density of the scatterer. Here, the approximation equation calculated by the approximation unit 432 is not limited to a linear expression, but a polynomial of a second or higher order may be used.

The feature calculating unit 43 can calculate a plurality of kinds of features by using parameters of a specimen calculated within a predetermined region of interest. More specifically, the feature calculating unit 43 calculates means and standard deviations of the slopes a, the intercepts b, and the mid-band fits c calculated by the approximation unit 432 for a plurality of unit areas set within a region of interest. The plurality of unit areas (also referred to as determination window) set within the region of interest has a same size (number of pixels). This size is set in advance by receiving a setting input using the input unit 6 and is stored in the storage unit 8. Hereinafter, as features calculated by the feature calculating unit 43, while the means and the standard deviations of the slopes a, the intercepts b, and the mid-band fits c are described as an example, statistics such as means, dispersions other than the standard deviations, and entropy may be applied.

Hereinafter, a mean and a standard deviation of the slopes a will be denoted as Mean S and Sd. S, the mean and the deviation of the intercepts b will be denoted as Mean I and Sd. I, and mean and the standard deviation of the mid-band fits c will be denoted as Mean M and Sd. M.

The classification unit 44 makes classification using a feature corresponding to a classification item selected in advance from among a plurality of kinds of features that can be calculated by the feature calculating unit 43 and assigns a color (hue) as visual information corresponding to a result of the classification to each pixel of an image generated based on an electric echo signal. The visual information assigned by the classification unit 44 to each pixel is not limited to the hue but may be any variable constituting a color space. As such a color space, for example, a Munsell color system in which brightness and saturation are added to the hue may be employed, and an RGB colorimetric system having R (red), G (green), and B (blue) as its variables may be employed.

The image processing unit 5 includes: a B-mode image data generating unit 51 that generates B-mode image data based on an echo signal; and a feature image data generating unit 52 that generates feature image data displaying information corresponding to the feature extracted by the feature calculating unit 43.

The B-mode image data generating unit 51 performs signal processing using known technologies such as a band pass filter, a logarithmic conversion, gain processing, and contrast processing for a digital signal and performs data decimation corresponding to a data step width determined according to the display range of an image in the display unit 7 and the like, thereby generating B-mode image data. The B-mode image is a grey scale image in which values of R (red), G (green), and B (blue) that are variables of a case where the RGB colorimetric system is employed as the color space match each other.

The feature image data generating unit 52 superimposes visual information assigned by the classification unit 44 to pixels on the pixels of an image of the B-mode image data, thereby generating feature image data. The feature image data generating unit 52, for example, assigns visual information corresponding to a feature of the frequency spectrum calculated based on an amplitude data group $F_j$ to a pixel area corresponding to a data amount of one amplitude data group $F_j$ (where j=1, 2, . . . , K) illustrated in FIG. 4.

The storage unit 8 includes a classification information storage unit 81. The classification information storage unit 81 stores information of classification results required for classifying the attribute of a tissue to be classified and for generating feature image data by the feature image data generating unit 52. In addition, the classification information storage unit 81 also stores information relating to the unit area used at the time of calculating a feature.

FIG. 7 is a diagram that schematically illustrates the classification information stored by the classification information storage unit 81. In a table Tb illustrated in FIG. 7, a classification purpose is assigned to the column of a classification item. In addition, for each classification item, an attribute of a tissue to be classified and a feature used for the classification are associated with each other. In each classification item, a color (hue) as visual information assigned to a pixel at the time of displaying a feature image and a value (range) of the feature are associated with each other. Hereinafter, classification items will be described more specifically for each classification item illustrated in FIG. 7 as an example.

(1) Case where Classification Item is Tumor Screening

The attributes of tissues to be classified (classification attributes) are a normal tissue and a malignant tumor tissue, and a feature used for the classification is the standard deviation Sd. M of the mid-band fit. In this case red is assigned to a pixel of which the value of the feature is 0≤Sd. M<$M_{11}$, and pink is assigned to a pixel corresponding to a tissue having $M_{11}$≤Sd. M<$M_{12}$. In contrast to this, a color is not assigned to a pixel of which the value of the feature is Sd. M≥$M_{12}$ (in FIG. 7, written as "Mask"). A tissue corresponding to a feature that is in a range for which a color is not assigned is a normal tissue. In this meaning, Sd. M=$M_{12}$ is a threshold used for separating a normal tissue and a malignant tumor tissue from each other. The association between a feature and a color, for example, is set according to the degree of a tumor in the malignant tumor tissue.

Figure 8:
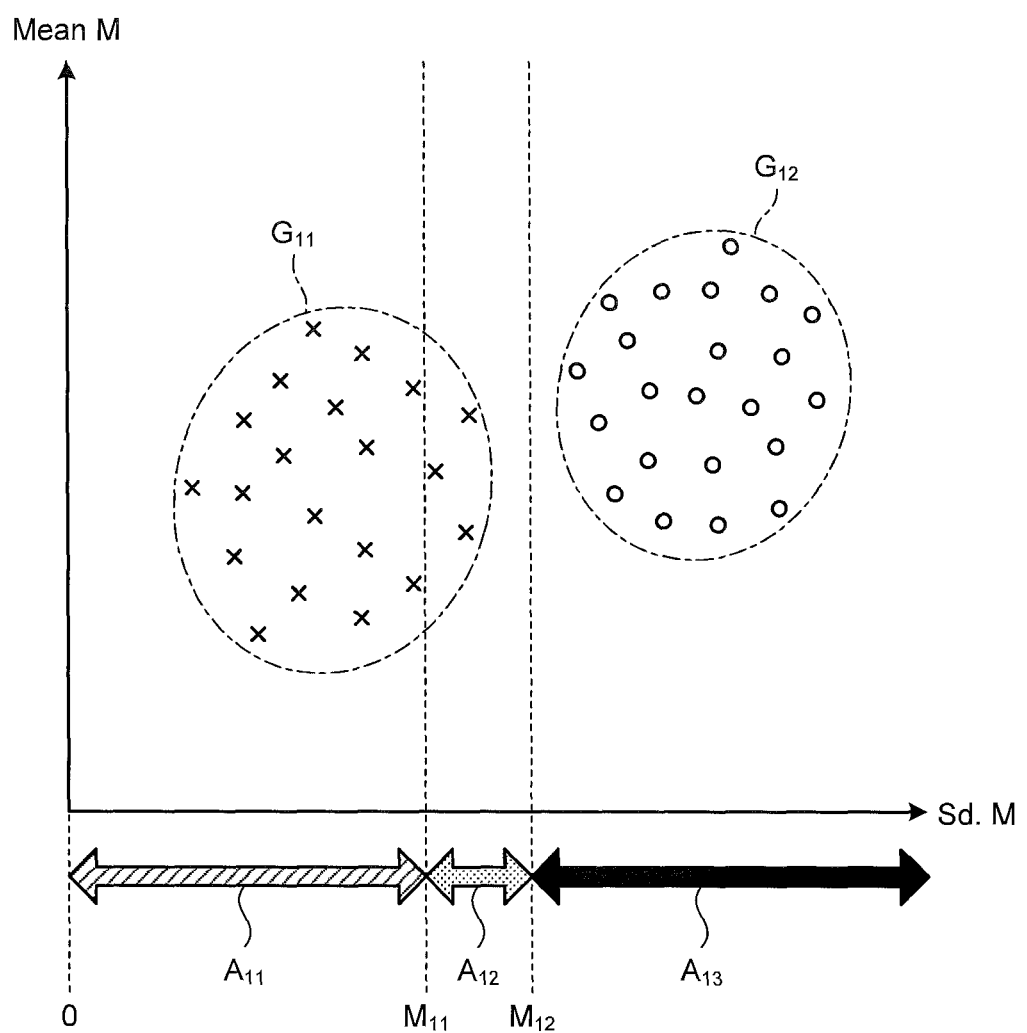
FIG. 8 is a diagram that schematically illustrates classifications and assignment of colors of a case where a classification item is tumor screening.

FIG. 8 is a diagram that schematically illustrates classifications and assignment of colors of a case where the classification item is tumor screening. FIG. 8 illustrates the feature distribution of known specimens in a feature space having the horizontal axis as the standard deviation Sd. M of the mid-band fit and having the vertical axis as the mean Mean M of the mid-band fit by using a scatter diagram and schematically illustrates a relation between the values of features and colors assigned to pixels. The known specimens are other specimens of which the attributes of the tissues are found in advance through a pathological examination or the like before a new specimen is examined in the first embodiment. In FIG. 8, an arrow $A_{11}$ represents the range of the feature Sd. M to which red is assigned, an arrow $A_{12}$ represents the range of the feature Sd. M to which pink is assigned, and an arrow $A_{13}$ represents the range of the feature Sd. M to which a color is not assigned.

In the feature space illustrated in FIG. 8, the known specimens are largely divided into two groups $G_{11}$ and $G_{12}$ based on the attributes. The group $G_{11}$ is a group of malignant tumor tissues, and the group $G_{12}$ is a group of normal tissues. The group $G_{11}$ and the group $G_{12}$ are clearly separate at Sd. M=$M_{12}$ in the direction of the horizontal axis Sd. M but are not separate in the direction of the vertical axis Mean M. In this way, in a case where the classification item is the tumor screening, by employing the standard deviation Sd. M of the mid-band fit as the feature, the attribute of the tissue of a specimen can be accurately classified.

The value of the mean Mean M of the mid-band fits corresponding to $M_{11}$ and $M_{12}$ described above, information of colors for the arrows $A_{11}$, $A_{12}$, and $A_{13}$, and information (hereinafter, referred to as a color table) associating the range of the Mean M and the visual information (the color and the mask) with each other are calculated by an external processing device (not illustrated in the drawings) or one or both of the feature calculating unit 43 and the classification unit 44 based on the distribution of a plurality of groups of known specimens, each of which has been found to belong to one of the attributes of a plurality of kinds of tissues through a pathological examination or the like before the start of the classification using features. Then, such information is stored in the classification information storage unit 81 in advance as a part of the classification information. When classification is started, the classification unit 44 reads the information from the classification information storage unit 81 and makes classification of the attributes of tissues.

(2) Case where Classification Item is Malignancy/Benignancy Distinction

The attributes of tissues to be classified are a malignant tumor tissue and a benign tumor tissue, and a feature used for the classification is the mean Mean M of the mid-band fits. In this case, a color is not assigned to a pixel of which the value of the feature is $0 \leq \text{Mean M} < M_{21}$. In contrast to this, blue is assigned to a pixel of which the value of the feature is $M_{21} \leq \text{Mean M} < M_{22}$, a water color is assigned to a pixel of which the value of the feature is $M_{22} \leq \text{Mean M} < M_{23}$, yellow is assigned to a pixel of which the value of the feature is $M_{23} \leq \text{Mean M} < M_{24}$, pink is assigned to a pixel of which the value of the feature is $M_{24} \leq \text{Mean M} < M_{25}$, and red is assigned to a pixel of which the value of the feature is Mean $M \geq M_{25}$.

Figure 9:
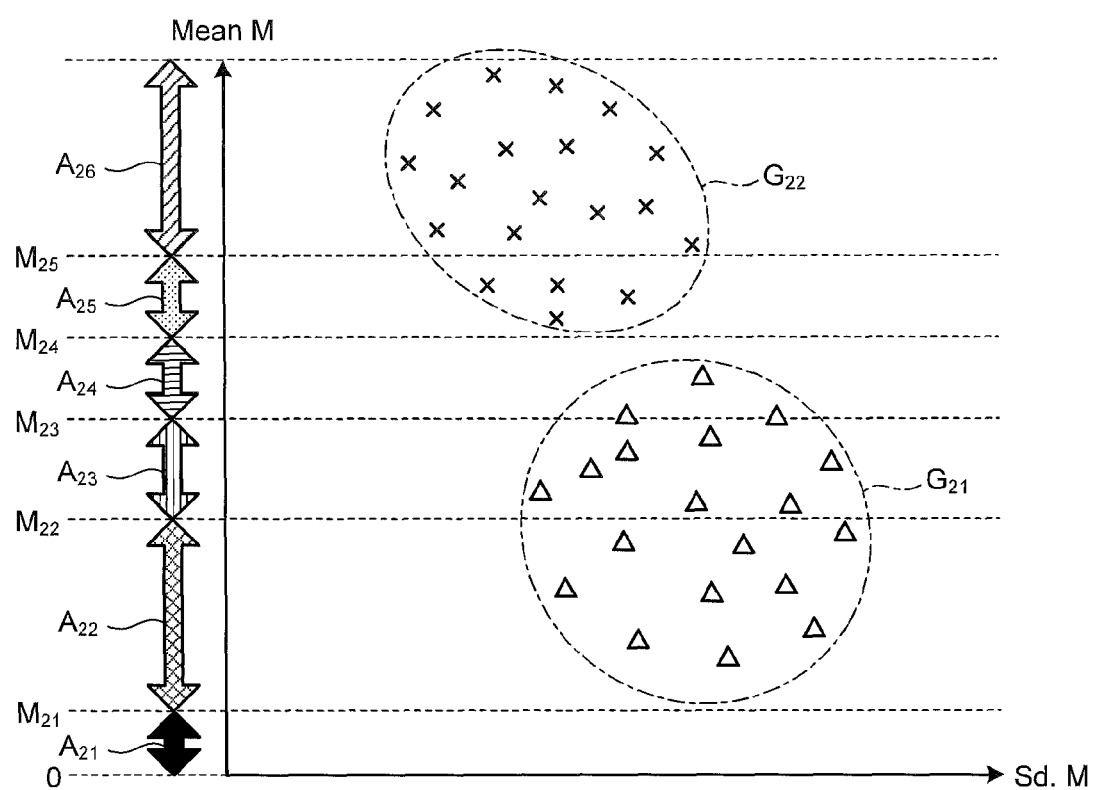
FIG. 9 is a diagram that schematically illustrates classifications and assignment of colors of a case where a classification item is a malignancy/benignancy distinction.

FIG. 9 is a diagram that schematically illustrates classifications and assignment of colors of a case where the classification item is a malignancy/benignancy distinction. FIG. 9 illustrates the feature distribution of known specimens in a feature space having the horizontal axis as the standard deviation Sd. M of the mid-band fit and having the vertical axis as the mean Mean M of the mid-band fit by using a scatter diagram and schematically illustrates a relation between the values of features and colors assigned to pixels. The known specimens are other specimens of which the attributes of the tissues are found in advance through a pathological examination or the like before a new specimen is examined in the first embodiment. In FIG. 9, an arrow $A_{21}$ represents a range to which a color is not assigned, an arrow $A_{22}$ represents a range to which blue is assigned, an arrow $A_{23}$ represents a range to which a water color is assigned, an arrow $A_{24}$ represents a range to which yellow is assigned, an arrow $A_{25}$ represents a range to which pink is assigned, and an arrow $A_{26}$ represents a range to which red is assigned.

In the feature space illustrated in FIG. 9, the known specimens are largely divided into two groups $G_{21}$ and $G_{22}$ based on the attributes. The group $G_{21}$ is a group of benign tumor tissues, and the group $G_{22}$ is a group of malignant tumor tissues. The group $G_{21}$ and the group $G_{22}$ are clearly separate at Mean $M=M_{24}$ in the direction of the vertical axis Mean M but are not separate in the direction of the horizontal axis Sd. M. In this way, in a case where the classification item is the malignancy/benignancy distinction, by employing the mean Mean M of the mid-band fits, the attribute of the tissue of a specimen can be accurately classified. In a case where the classification item is the malignancy/benignancy distinction, it is preferable that a malignant tumor tissue and a benign tumor tissue are displayed to be identifiable in a feature image. For this reason, in the case illustrated in FIG. 9, different colors are assigned to the groups $G_{21}$ and $G_{22}$.

The value of the mean Mean M of the mid-band fits corresponding to $M_{21}$, $M_{22}$, $M_{23}$, $M_{24}$, and $M_{25}$ described above, information of colors for the arrows $A_{21}$, $A_{22}$, $A_{23}$, $A_{24}$, $A_{25}$, and $A_{26}$, and information (hereinafter, referred to as a color table) associating the range of the Mean M and the visual information (the color and the mask) with each other are calculated by an external processing device (not illustrated in the drawings) or one or both of the feature calculating unit 43 and the classification unit 44 based on the distribution of a plurality of groups of known specimens, each of which has been found to belong to one of the attributes of a plurality of kinds of tissues through a pathological examination or the like before the start of the classification using features. Then, such information is stored in the classification information storage unit 81 in advance as a part of the classification information. When classification is started, the classification unit 44 reads the information from the classification information storage unit 81 and makes classification of the attributes of tissues.

(3) Case where Classification Item is Follow-Up Determination 1

The attributes of tissues to be classified are a follow-up-required tissue and a benign tumor tissue, and a feature used for the classification is the standard deviation Sd. I of the intercept. In this case, red is assigned to a pixel of which the value of the feature is $0 \leq \text{Sd. I} < I_1$, pink is assigned to a pixel of $I_1 \leq \text{Sd. I} < I_2$, a water color is assigned to a pixel of $I_2 \leq \text{Sd. I} < I_3$, and blue is assigned to a pixel of $I_3 \leq \text{Sd. I} < I_4$. In contrast to this, a color is not assigned to a pixel of which the value of the feature is Sd. $I \geq I_4$.

Figure 10:
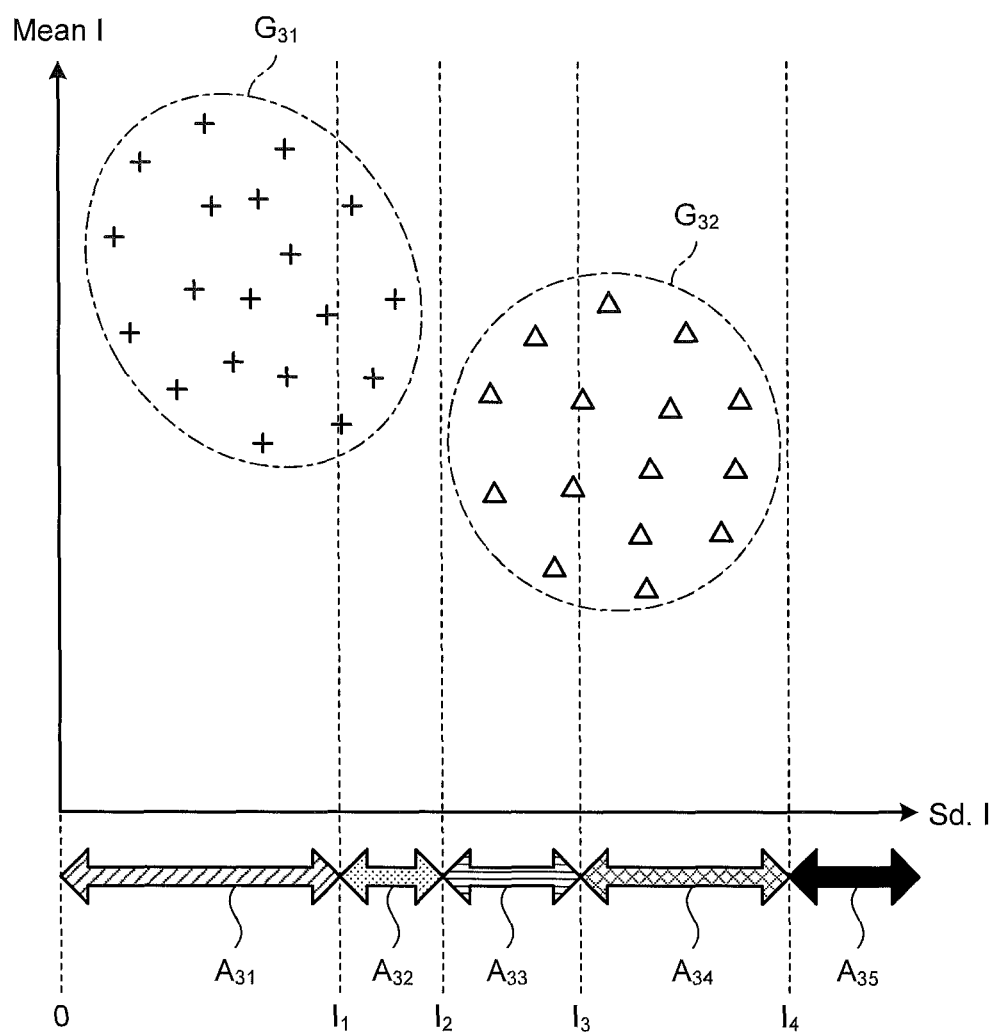
FIG. 10 is a diagram that schematically illustrates classifications and assignment of colors of a case where a classification item is a follow-up determination 1.

FIG. 10 is a diagram that schematically illustrates classifications and assignment of colors of a case where the classification item is the follow-up determination 1. FIG. 10 illustrates the feature distribution of known specimens in a feature space having the horizontal axis as the standard deviation Sd. I of the intercept and having the vertical axis as the mean Mean I of the intercepts by using a scatter diagram and schematically illustrates a relation between the values of features and colors assigned to pixels. The known specimens are other specimens of which the attributes of the tissues are found in advance through a pathological examination or the like before a new specimen is examined in the first embodiment. In FIG. 10, an arrow $A_{31}$ represents a range to which red is assigned, an arrow $A_{32}$ represents a range to which pink is assigned, an arrow $A_{33}$ represents a range to which a water color is assigned, an arrow $A_{34}$ represents a range to which blue is assigned, and an arrow $A_{35}$ represents a range to which a color is not assigned.

In the feature space illustrated in FIG. 10, the known specimens are largely divided into two groups $G_{31}$ and $G_{32}$ based on the attributes. The group $G_{31}$ is a group of follow-up-required tissues, and the group $G_{32}$ is a group of benign tumor tissues. The group $G_{31}$ and the group $G_{32}$ are clearly separate at Sd. $I=I_2$ in the direction of the horizontal axis Sd. I but are not separate in the direction of the vertical axis Mean I. In this way, in a case where the follow-up determination 1 is performed, by employing the standard deviation Sd. I of the intercept, the attribute of the tissue of a specimen can be accurately classified. In a case where the classification item is the follow-up determination 1, it is preferable that a follow-up-required tissue and a benign tumor tissue are displayed to be identifiable in a feature image. For this reason, in the case illustrated in FIG. 10, different colors are assigned to the groups $G_{31}$ and $G_{32}$.

The value of the standard deviation Sd. I of intercepts corresponding to $I_1$, $I_2$, $I_3$, and $I_4$ described above, information of colors for the arrows $A_{31}$, $A_{32}$, $A_{33}$, $A_{34}$, and $A_{35}$, and information (a color table) associating the range of the standard deviation Sd. I and the visual information (the color and the mask) with each other are calculated by an external processing device (not illustrated in the drawings) or one or both of the feature calculating unit 43 and the classification unit 44 based on the distribution of a plurality of groups of known specimens, each of which has been found to belong to one of the attributes of a plurality of kinds of tissues through a pathological examination or the like before the start of the classification using features. Then, such information is stored in the classification information storage unit 81 in advance as a part of the classification information. When classification is started, the classification unit 44 reads the information from the classification information storage unit 81 and makes classification of the attributes of tissues.

(4) Case where Classification Item is Follow-Up Determination 2

The attributes of tissues to be classified are a follow-up-required tissue and a malignant tumor tissue, and a feature used for the classification is d(Mean M, Sd. I) (hereinafter, simply referred to as "d") calculated as a function of the mean Mean M of mid-band fits and the standard deviation Sd. I of intercepts. More specifically, this d is defined as a linear combination of two features Mean M and Sd. I. In this case, red is assigned to a pixel of which the value of the feature d is $0 \leq d < d_1$, pink is assigned to a pixel of $d_1 \leq d < d_2$, and green is assigned to a pixel of $d_2 \leq d < d_3$, and yellow is assigned to a pixel of $d_3 \leq d < d_4$. In contrast to this, a color is not assigned to a pixel of which the value of the feature is $d \geq d_4$.

Figure 11:
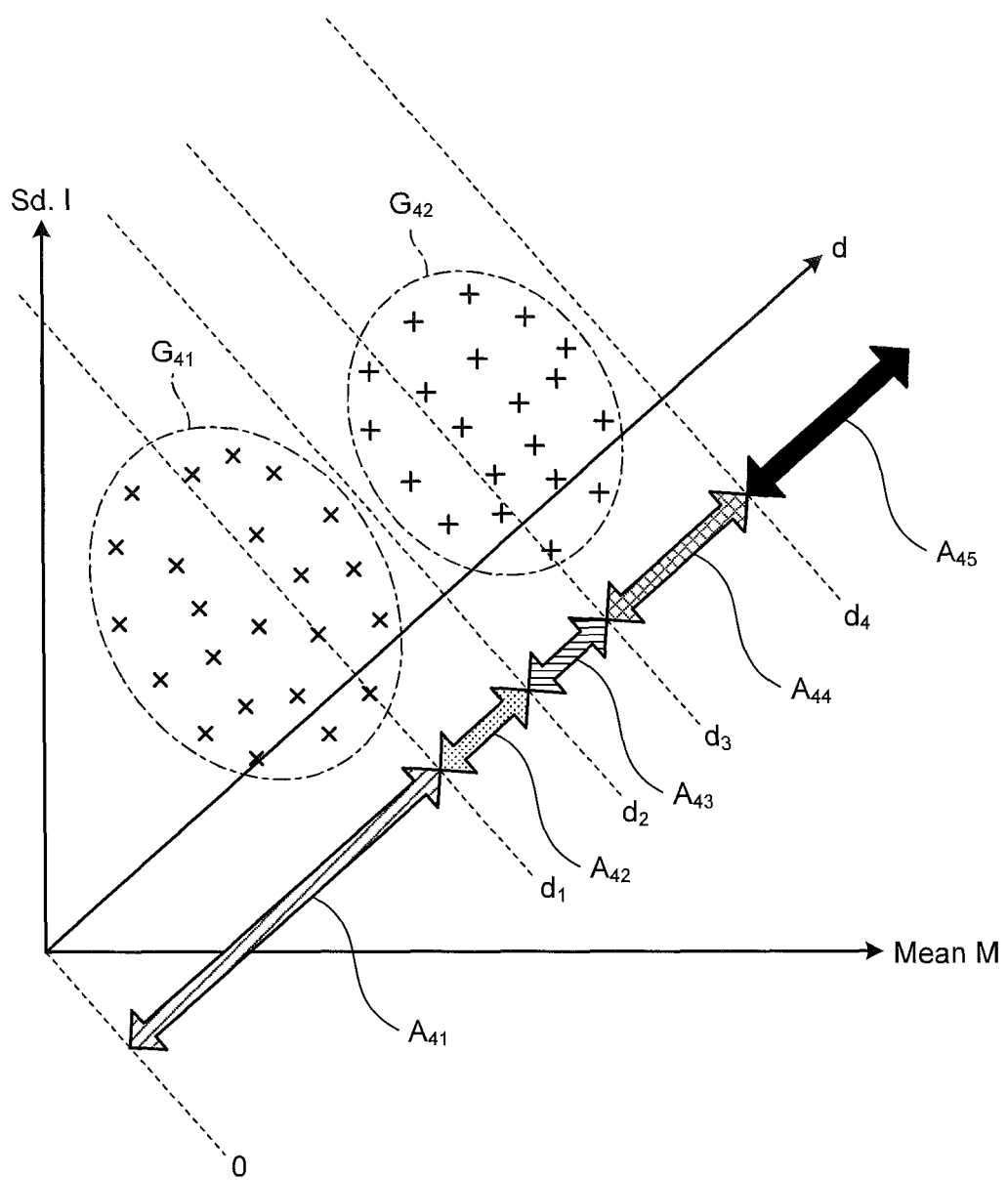
FIG. 11 is a diagram that schematically illustrates classifications and assignment of colors of a case where a classification item is a follow-up determination 2.

FIG. 11 is a diagram that schematically illustrates classifications and assignment of colors of a case where the classification item is the follow-up determination 2. FIG. 11 illustrates the feature distribution of known specimens in a feature space having the horizontal axis as the mean Mean M of the mid-band fits and having the vertical axis as the standard deviation Sd. I of the intercepts by using a scatter diagram and schematically illustrates a relation between the values of features and colors assigned to pixels. The known specimens are other specimens of which the attributes of the tissues are found in advance through a pathological examination or the like before a new specimen is examined in the first embodiment. In FIG. 11, an arrow $A_{41}$ represents a range to which red is assigned, an arrow $A_{42}$ represents a range to which pink is assigned, an arrow $A_{43}$ represents a range to which green is assigned, an arrow $A_{44}$ represents a range to which yellow is assigned, and an arrow $A_{45}$ represents a range to which a color is not assigned.

In the feature space illustrated in FIG. 11, the known specimens are largely divided into two groups $G_{41}$ and $G_{42}$ based on the attributes. The group $G_{41}$ is a group of follow-up-required tissues, and the group $G_{42}$ is a group of malignant tumor tissues. The group $G_{41}$ and the group $G_{42}$ are clearly separate at $d=d_2$ in the direction of an axis d that is an axis other than the horizontal axis Mean M and the vertical axis Sd. I and intersects with the horizontal axis Mean M and the vertical axis Sd. I at the origin but are not separate in the directions of the horizontal axis Mean M and the vertical axis Sd. I. Here, the value of a feature d is defined as a distance from the origin along the axis d. In this way, in a case where classification item is the follow-up determination 2, by employing the feature d(Mean M, Sd. I) that is a linear combination of the mean Mean M of mid-band fits and the standard deviation Sd. I of intercepts, the attribute of the tissue of a specimen can be accurately classified. In a case where the classification item is the follow-up determination 2, it is preferable that a follow-up-required tissue and a benign tumor tissue are displayed to be identifiable in a feature image. For this reason, in the case illustrated in FIG. 11, different colors are assigned to the groups $G_{41}$ and $G_{42}$.

The ratios (in other words in the direction of the axis d) of the mean Mean M of mid-band fits and the standard deviation Sd. I of intercepts to the feature d, the values of features d corresponding to $d_1$, $d_2$, $d_3$, and $d_4$ described above, information of colors for the arrows $A_{41}$, $A_{42}$, $A_{43}$, $A_{44}$, and $A_{45}$, and information (color table) associating the ranges of d and visual information (the color and the mask) are calculated by an external processing device (not illustrated in the drawings) or one or both of the feature calculating unit 43 and the classification unit 44 based on the distribution of a plurality of groups of known specimens, each of which has been found to belong to one of the attributes of a plurality of kinds of tissues through a pathological examination or the like before the start of the classification using features. Then, such information is stored in the classification information storage unit 81 in advance as a part of the classification information. When classification is started, the classification unit 44 reads the information from the classification information storage unit 81 and makes classification of the attributes of tissues.

In addition to the information described above, for example, the storage unit 8 stores information (the relation between the amplification factor and the reception depth illustrated in FIG. 2) that is necessary for the amplification process, information (the relation between the amplification factor and the reception depth illustrated in FIG. 3) that is necessary for the amplification correction process, information (see Equation (1)) that is necessary for the attenuation correction process, and information of a window function (Hamming, Hanning, Blackman, or the like) that is necessary for the frequency analyzing process.

In addition, the storage unit 8 stores an operation program used for performing a method of operating the ultrasound observation apparatus 1 (medical diagnostic apparatus). This operation program may be recorded on a computer-readable recording medium such as a hard disk, a flash memory, a CD-ROM, a DVD-ROM, or a flexible disk and be broadly distributed. The recording of various programs on a recording medium or the like may be performed when a computer or a recording medium is shipped as a product or may be performed by downloading the program through a communication network.

The storage unit 8 having the configuration described above is realized by using a read only memory (ROM) in which various programs and the like are installed in advance, a random access memory (RAM) that stores a calculation parameter, data, and the like of each process, and the like. The various programs described above may be acquired by downloading them through a communication network. The communication network described here, for example, is realized by a public network, a local area network (LAN), a wide area network (WAN), or the like in a wired or wireless manner.

The control unit 9 is realized by a central processing unit (CPU) having a calculation and control function, various calculation circuits, and the like. By reading information stored by the storage unit 8 and various programs including the operation program of the ultrasound observation apparatus 1 from the storage unit 8, the control unit 9 performs various calculation processes relating to the method of operating the ultrasound observation apparatus 1, thereby performing overall control of the ultrasound observation apparatus 1. In addition, the control unit 9 and the computation unit 4 may be configured using a common CPU and the like.

Figure 12:
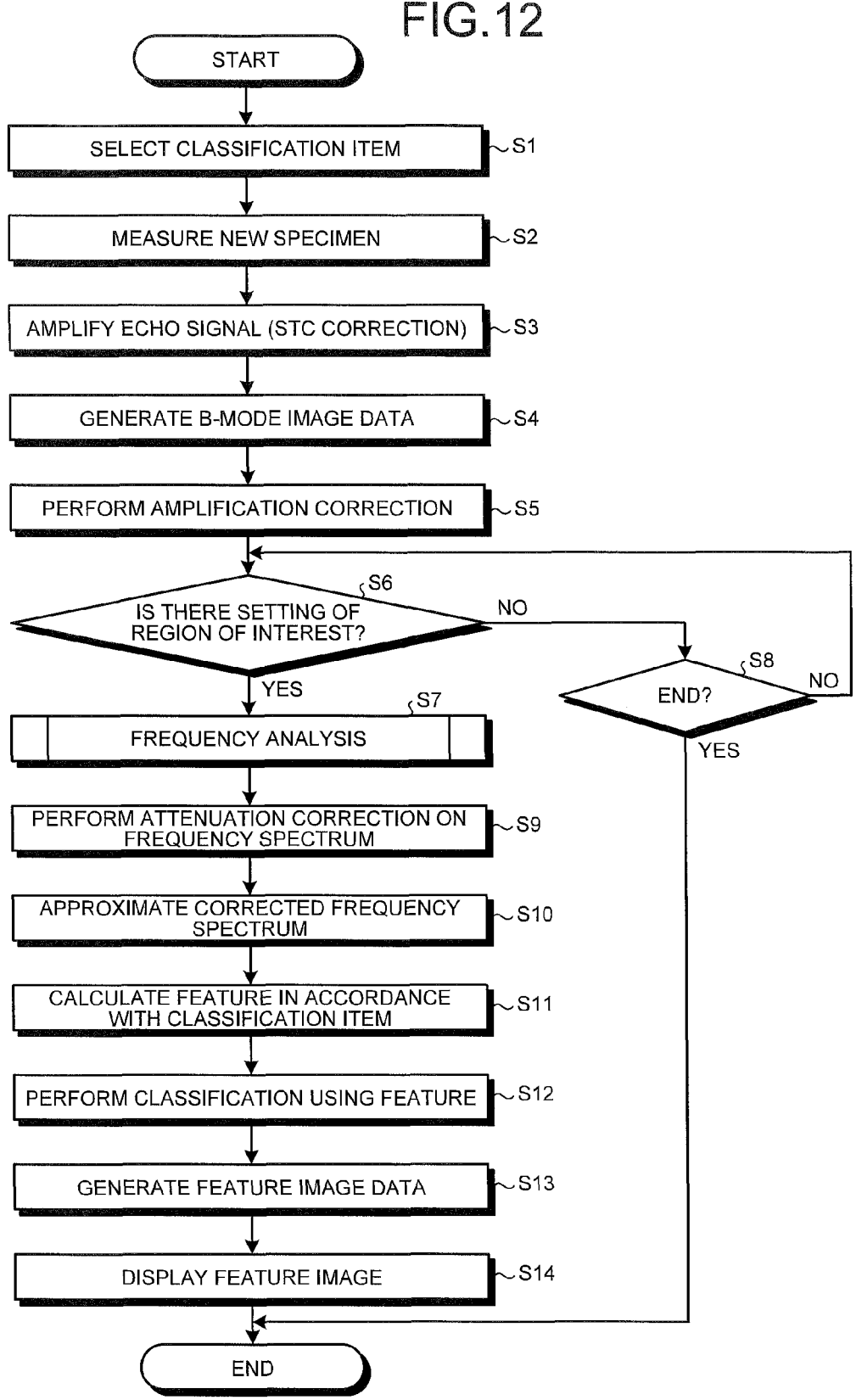
FIG. 12 is a flowchart that illustrates an overview of a process performed by the ultrasound observation apparatus according to the first embodiment of the present invention.

FIG. 12 is a flowchart that illustrates an overview of a process performed by the ultrasound observation apparatus 1 having the configuration as described above. First, the input unit 6 receives a selection input of a classification item (Step S1). FIG. 13 is a diagram that illustrates an example of the display of a selection screen displayed by the display unit 7 when the input unit 6 receives a selection input of the classification item. On a selection screen 101 illustrated in FIG. 13, classification items and the attributes of tissues to be classified (classification attributes) are displayed. On the selection screen 101, a framed cursor 102 representing a classification item that is currently selected is displayed. FIG. 13 illustrates a state in which the "tumor screening" is selected as the classification item. A user, after moving the framed cursor 102 to a desired classification item by using a mouse or the like, clicks on the classification item by using the mouse so as to finalize the selection, thereby completing the selection input. The input unit 6 outputs a received selection input signal to the control unit 9.

Subsequently, the ultrasound observation apparatus 1, first, performs measurement on a new specimen by using the ultrasound probe 2 (Step S2). More specifically, the ultrasound transducer 21 of the ultrasound probe 2 converts an electric pulse signal into an ultrasonic pulse and sequentially transmits the converted ultrasonic pulses to the specimen. The ultrasonic pulses are reflected from the specimen, and ultrasound echoes are generated. The ultrasound transducer 21 converts the ultrasound echoes into electric echo signals. At this time, the frequency band of the pulse signal may be a broad band that almost covers a linear response frequency band of the electroacoustic conversion from a pulse signal to an ultrasonic pulse that is performed by the ultrasound transducer 21. Accordingly, in an approximation process of the frequency spectrum to be described later, approximation having high accuracy can be performed.

The signal amplifying unit 31 that has received an echo signal from the ultrasound probe 2 amplifies the echo signal (Step S3). Here, the signal amplifying unit 31 performs amplification (STC correction) on the echo signal, for example, based on the relation between the amplification factor and the reception depth illustrated in FIG. 2. At this time, the frequency band of various processes for the echo signal that are performed by the signal amplifying unit 31 may be a broadband that almost covers the linear response frequency band of the acoustoelectric conversion from an ultrasound echo to an echo signal that is performed by the ultrasound transducer 21. This is also for enabling approximation having high accuracy in the approximation process of the frequency spectrum to be described later.

Subsequently, the B-mode image data generating unit 51 generates B-mode image data using an echo signal that has been amplified by the signal amplifying unit 31 (Step S4). In addition, after this Step S4, the control unit 9 may perform control for displaying a B-mode image corresponding to the generated B-mode image data on the display unit 7.

The amplification correction unit 41 performs an amplification correction on a signal output from the transmitting and receiving unit 3 such that the amplification factor is constant regardless of the reception depth (Step S5). Here, the amplification correction unit 41 performs the amplification correction, for example, based on the relation between the amplification factor and the reception depth illustrated in FIG. 3.

Thereafter, in a case where a region of interest is set through the input unit 6 (Step S6: Yes), the frequency analyzing unit 42 calculates a frequency spectrum by performing a frequency analysis through an FFT operation (Step S7). In this Step S7, all the area of the image may be set as a region of interest. On the other hand, in a case where the region of interest is not set (Step S6: No), when an input of an instruction for ending the process is received by the input unit 6 (Step S8: Yes), the ultrasound observation apparatus 1 ends the process. On the other hand, in a case where the region of interest is not set (Step S6: No), when the input unit 6 does not receive an input of an instruction for ending the process (Step S8: No), the ultrasound observation apparatus 1 returns the process to Step S6.

Figure 14:
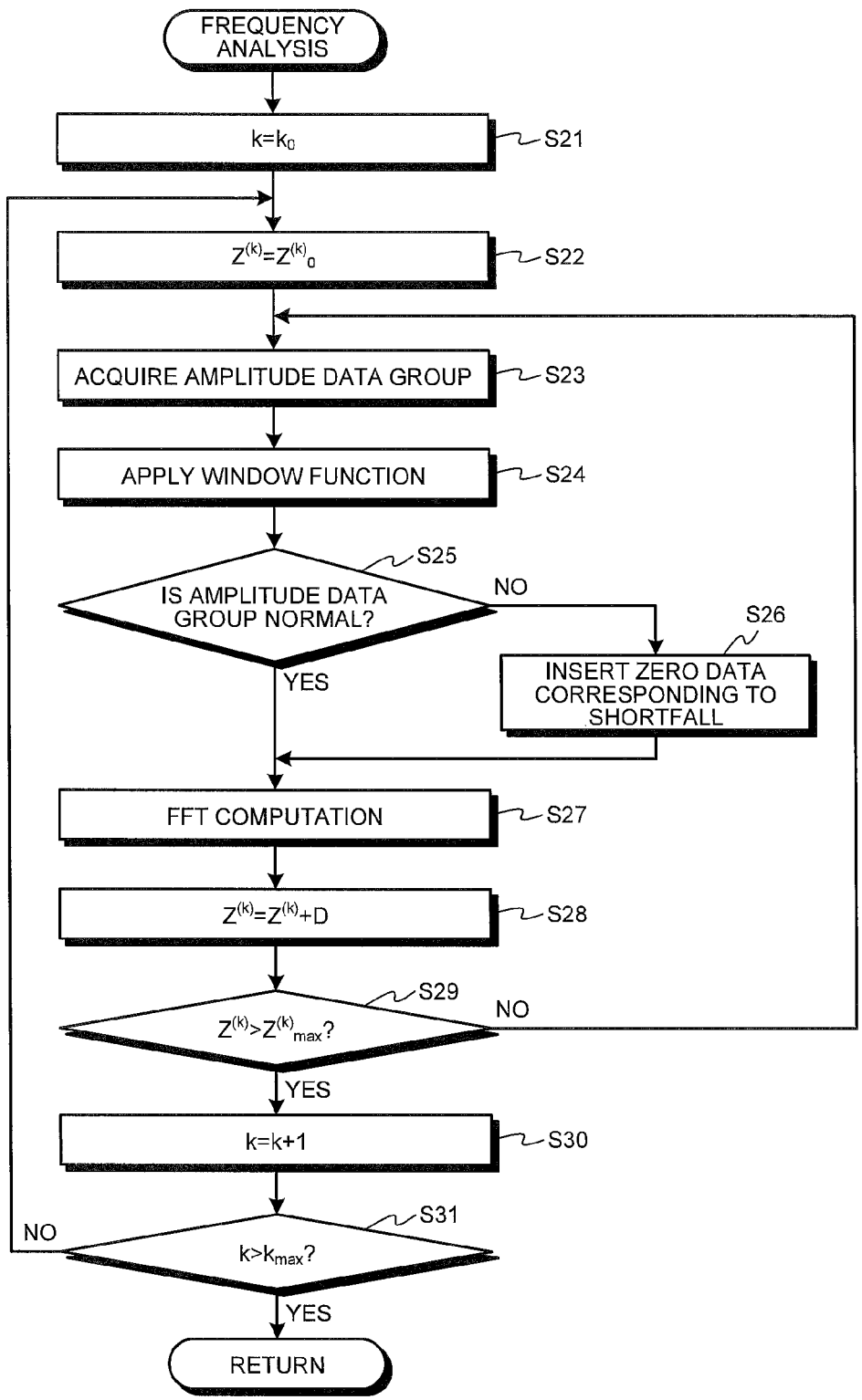
FIG. 14 is a flowchart that illustrates an overview of a process performed by the frequency analyzing unit of the ultrasound observation apparatus according to the first embodiment of the present invention.

FIG. 14 is a flowchart that illustrates an overview of a process performed by the frequency analyzing unit 42 in Step S7. Hereinafter, the frequency analyzing process will be described in detail with reference to the flowchart illustrated in FIG. 14. First, the frequency analyzing unit 42 sets a counter k used for identifying a sound ray to be analyzed to $k_0$ (Step S21).

Subsequently, the frequency analyzing unit 42 sets the initial value $Z^{(k)}_0$ of a data position (corresponding to the reception depth) $Z^{(k)}$ representing a series of data groups (amplitude data groups) acquired for an FFT operation (Step S22). For example, FIG. 4 illustrates a case where the first data position of the sound ray $SR_k$ is set as the initial value $Z^{(k)}_0$ as described above.

Thereafter, the frequency analyzing unit 42 acquires an amplitude data group to which the data position $Z^{(k)}$ belongs (Step S23) and applies a window function stored in the storage unit 8 to the acquired amplitude data group (Step S24). In this way, by operating the window function for the amplitude data group, the discontinuation of the amplitude data group on the boundary is avoided, and the occurrence of an artifact can be prevented.

Subsequently, the frequency analyzing unit 42 determines whether or not the amplitude data group of the data position $Z^{(k)}$ is a normal data group (Step S25). As described with reference to FIG. 4, the amplitude data group needs to have data of a number of exponent of two. Hereinafter, the number of data of a normal amplitude data group is assumed to be $2^n$ (where n is a positive integer). In the first embodiment, the data position $Z^{(k)}$ is set to be the center of the amplitude data group to which the data position $Z^{(k)}$ belongs as possibly as can. More specifically, since the number of data included in the amplitude data group is $2^n$, the data position $Z^{(k)}$ is set to a $2^n/2$ ($=2^{n-1}$)-th position near the center of the amplitude data group. In other words, in a case where an amplitude data group is normal, it means that $2^{n-1}-1$ ($=N$) pieces of data are present to the front side of the data position $Z^{(k)}$, and $2^{n-1}$ ($=M$) pieces of data are present to the rear side of the data position Z. In the case illustrated in FIG. 4, both amplitude data groups $F_2$ and $F_3$ are normal. FIG. 4 illustrates a case of n=4 (N=7 and M=8) as an example.

In Step S25, as a result of the determination, in a case where the amplitude data group of the data position $Z^{(k)}$ is normal (Step S25: Yes), the frequency analyzing unit 42 proceeds to Step S27 to be described later.

On the other hand, as a result of the determination acquired in Step S25, in a case where the amplitude data group of the data position $Z^{(k)}$ is not normal (Step S25: No), the frequency analyzing unit 42 inserts zero data corresponding to a shortfall to generate a normal amplitude data group (Step S26). A window function is operated for an amplitude data group (for example, amplitude data groups $F_1$ and $F_k$ illustrated in FIG. 4) determined not to be normal in Step S25 before the insertion of the zero data. For this reason, also in a case where the zero data is inserted into the amplitude data group, discontinuation of the data does not occur. After Step S26, the frequency analyzing unit 42 proceeds to Step S27 to be described later.

In Step S27, the frequency analyzing unit 42 performs an FFT computation by using the amplitude data group, thereby acquiring a frequency spectrum that is a frequency distribution of amplitudes (Step S27). This result, for example, is illustrated in FIG. 5.

Subsequently, the frequency analyzing unit 42 changes the data position $Z^{(k)}$ by a step width D (Step S28). The step width D is assumed to be stored in the storage unit 8 in advance. FIG. 4 illustrates a case of D=15. Although it is desirable that the step width D matches the data step width used when the B mode image data is generated by the B-mode image data generating unit 51, in a case where the amount of calculation performed in the frequency analyzing unit 42 is desired to be decreased, a value larger than the data step width may be set as the step width D.

Thereafter, the frequency analyzing unit 42 determines whether or not the data position $Z^{(k)}$ is larger than a maximum value $Z^{(k)}{}_{max}$ of the sound ray $SR_k$ (Step S29). In a case where the data position $Z^{(k)}$ is larger than the maximum value $Z^{(k)}{}_{max}$ (Step S29: Yes), the frequency analyzing unit 42 increases the counter k by one (Step S30). This represents that the process is moved to a next sound ray. On the other hand, in a case where the data position $Z^{(k)}$ is the maximum value $Z^{(k)}{}_{max}$ or less (Step S29: No), the frequency analyzing unit 42 causes the process to be returned to Step S23. In this way, the frequency analyzing unit 42 performs, on the sound ray $SR_k$, an FFT operation for $[(Z^{(k)}{}_{max}-Z^{(k)}{}_0+1)/D+1]$ amplitude data groups. Here, [X] represents a maximum integer not exceeding "X".

After Step S30, the frequency analyzing unit 42 determines whether or not the counter k is larger than the maximum value $k_{max}$ (Step S31). In a case where the counter k is larger than the $k_{max}$ (Step S31: Yes), the frequency analyzing unit 42 ends the series of FFT processes. On the other hand, in a case where the counter k is the $k_{max}$ or less (Step S31: No), the frequency analyzing unit 42 causes the process to be returned to Step S22.

In this way, the frequency analyzing unit 42 performs an FFT operation a plurality of number of times on each of $(k_{max}-k_0+1)$ sound rays within the region of interest.

Thereafter, the attenuation correction unit 431 performs an attenuation correction on the frequency spectrum calculated by the frequency analyzing unit 42 (Step S9). By performing the correction process of adding the attenuation amount A of Equation (1) described above to the intensity I for all the frequencies f, the attenuation correction unit 431 acquires a new frequency spectrum. Accordingly, the frequency spectrum from which the influence of the attenuation associated with the propagation of an ultrasound wave is reduced can be acquired. The frequency spectrum $C_2$ illustrated in FIG. 6 is a curve that is acquired as a result of performing the attenuation correction process for the frequency spectrum $C_1$.

Subsequently, the approximation unit 432 approximates the attenuation-corrected frequency spectrum (corrected frequency spectrum) by a linear expression by performing a regression analysis at a predetermined frequency band (Step S10). In this approximation process, the approximation unit 432 calculates a slope a, an intercept b, and a mid-band fit c as parameters that are necessary for the calculation of a feature and writes and stores the calculated parameters into the classification information storage unit 81.

Thereafter, the feature calculating unit 43 calculates a feature that is necessary for the classification in accordance with the classification item selected in Step S1 by referring to the classification information storage unit 81 (Step S11). For example, in a case where the tumor screening is selected as the classification item, as illustrated in FIG. 7, the feature calculating unit 43 calculates the standard deviation Sd. M of the mid-band fits acquired for the unit areas within the region of interest.

The classification unit 44 classifies the attributes of tissues using the features calculated by the feature calculating unit 43 and assigns a color corresponding to the result of the classification to each pixel disposed within the region of interest (Step S12). The assignment of the color, for example, as described with reference to FIGS. 8 to 11, is determined based on the value of the feature determined according to the classification item and is performed for each unit area.

The feature image data generating unit 52 superimposes colors as visual information on the pixels of the B-mode image data generated by the B-mode image data generating unit 51 based on the color assignment information of the pixels transmitted from the classification unit 44 through the control unit 9, thereby generating feature image data (Step S13).

Thereafter, the display unit 7, under the control of the control unit 9, displays a feature image corresponding to the feature image data generated by the feature image data generating unit 52 (Step S14).

Figure 15:
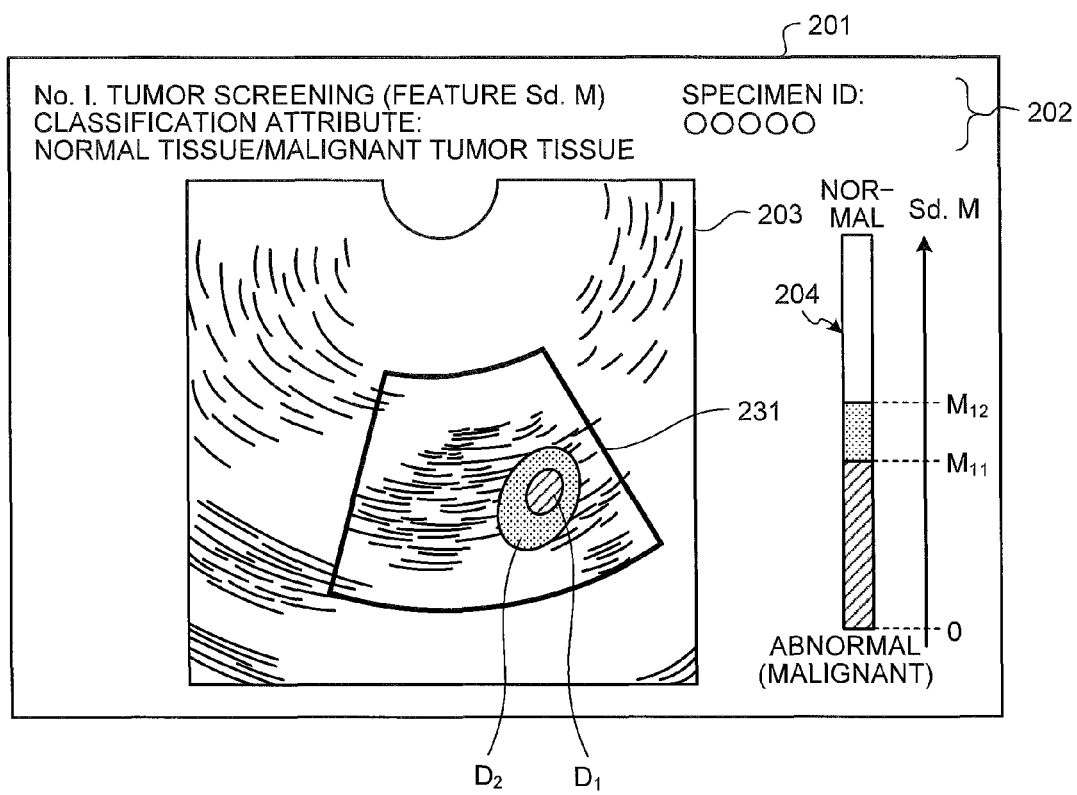
FIG. 15 is a diagram that schematically illustrates an example of the display of a feature image in the display unit of the ultrasound observation apparatus according to the first embodiment of the present invention.

FIG. 15 is a diagram that schematically illustrates an example of the display of a feature image in the display unit 7. A feature image 201 illustrated in FIG. 15 includes an examination content display region 202, an image display region 203, and a color feature display region 204.

The examination content display region 202 is disposed in an upper portion of the screen and displays information of a classification item, a feature used for the classification, a classification attribute, a specimen ID, terms (to be described later) representing the classification attribute for both polarities of a color bar, and the like. FIG. 15 illustrates a case where the classification item is the tumor screening as an example.

The image display region 203 displays a composite image acquired by superimposing colors based on the classification result on the pixels of the B-mode image. The image display region 203 displays a region 231 of interest and displays the attribute of the inside of the region 231 of interest using a corresponding color. In FIG. 15, a red area $D_1$ and a pink area $D_2$ are displayed as malignant tumor tissues.

The color feature display region 204 displays a color bar that represents a relation between the color displayed in the image display region 203 and the value of the feature.

At both upper and lower polarities of the color bar, terms corresponding to corresponding classification attributes are displayed. When the classification item is "No. 1: Tumor Screening", as illustrated in FIG. 15, "Normal"/"Abnormal (Malignant)" are displayed. On the other hand, when the classification item is "No. II: Malignancy/Benignancy Distinction", "Benignancy"/"Malignancy" are displayed, when the classification item is "No. III: Follow-up Determination 1", "Benignancy"/"Observation Required" are displayed, and, when the classification item is "No. IV: Follow-up Determination 2", "Observation Required"/"Malignancy" are displayed. The terms representing the polarities of the color bar and information representing a correspondence relation between these terms and the classification item are also stored in the classification information storage unit 81 in advance as a part of the classification information before the classification using the feature is started. When the classification is started, the image processing unit 5 reads these from the classification information storage unit 81 and classifies the attribute of a tissue.

In the series of processes (Steps S1 to S14) described as above, it may be configured such that the process of Step S4 and the process of Steps S5 to S14 are performed together, and the B-mode image and the feature image are displayed together.

According to the first embodiment of the present invention described above, a plurality of kinds of features are calculated based on a received signal from a specimen, the attributes of a tissue of the specimen are classified using a feature determined according to a classification item selected in advance from among the plurality of features, and feature image data in which visual information corresponding to a result of the classification is assigned to each pixel of the image based on the received signal is generated. Accordingly, when the attributes of a tissue are classified, only a feature optimal to the classification of the attribute can be used without using all the features, and image data in which tissues are classified according to the contents of diagnoses can be efficiently generated.

In addition, according to the first embodiment, by assigning colors as the visual information, a user can clearly identify the attribute of a tissue of a specimen.

Furthermore, according to the first embodiment, also when features of known specimens are acquired, the attributes are classified using features acquired by performing an attenuation correction of the frequency spectrum acquired through a frequency analysis. Accordingly, compared to a case where features calculated without performing the attenuation correction are used, the areas of groups can be acquired in a state of being more clearly divided in the feature space, and different attributes can be distinguished.

Second Embodiment

In the first embodiment of the present invention, the domain of the frequency feature, the visual information (the color and the mask) corresponding to the domain, and information (color table) associating the domain and the visual information with each other, which are necessary for the classification, are stored in the classification information storage unit 81 in advance as a part of the classification information. In the first embodiment, all the classification information is information derived from specimens of which the attributes of the tissues are clear through a pathological examination or the like before the classification performed by the classification unit 44. A medical diagnostic apparatus according to a second embodiment of the present invention has a function for updating classification information while accumulating features of regions to be examined in specimens of which the attributes of tissues to be examined are found through a pathological examination and the like as known specimen information.

Figure 16:
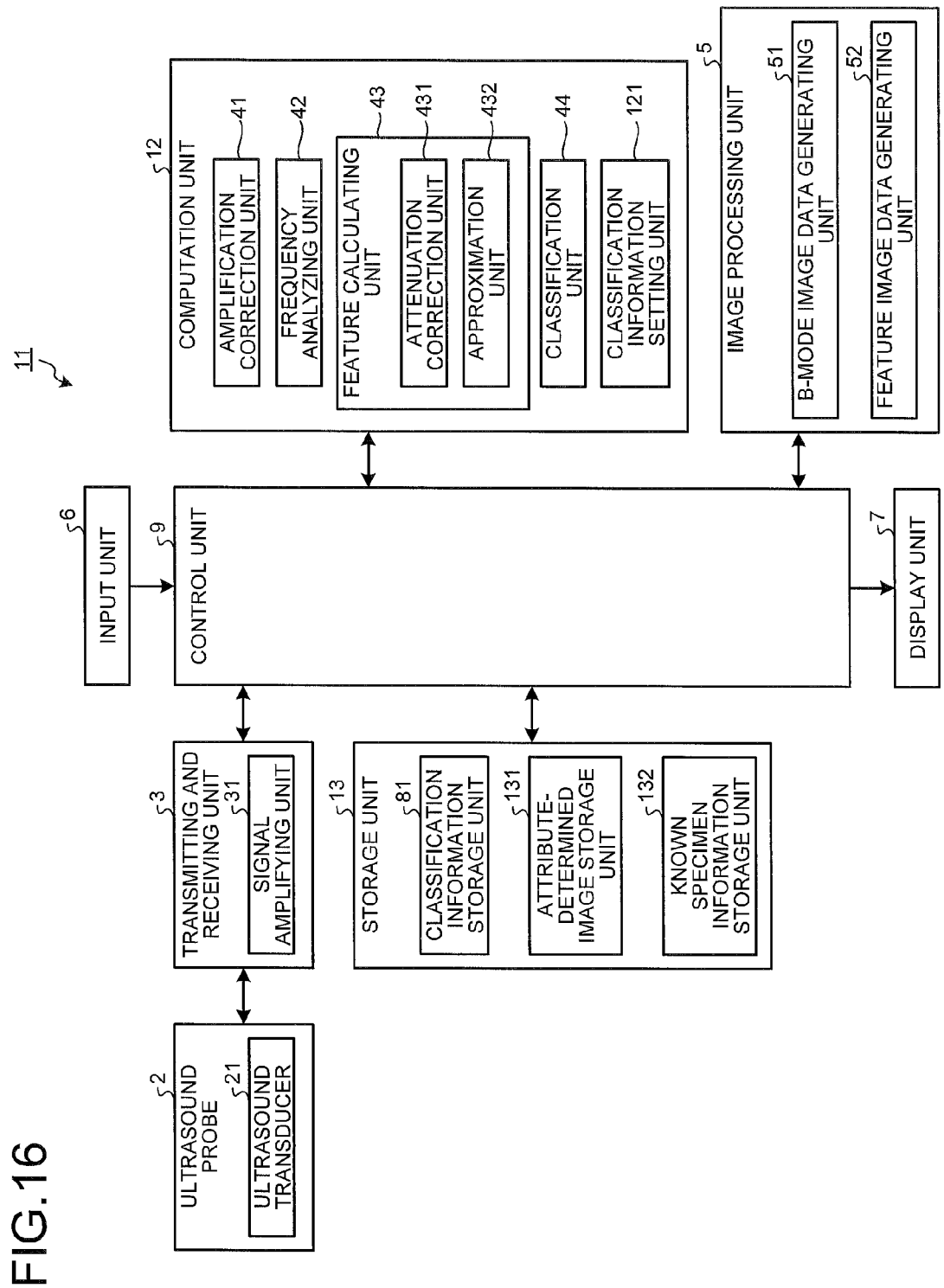
FIG. 16 is a block diagram that illustrates the configuration of an ultrasound observation apparatus according to a second embodiment of the present invention.

FIG. 16 is a block diagram that illustrates the configuration of an ultrasound observation apparatus that is a medical diagnostic apparatus according to the second embodiment of the present invention. An ultrasound observation apparatus 11 illustrated in FIG. 16 has the same configuration as that of the ultrasound observation apparatus 1 described in the first embodiment except for a computation unit 12 and a storage unit 13. For this reason, the same reference signs are used to designate the same elements as those of the ultrasound observation apparatus 1.

The computation unit 12 includes: an amplification correction unit 41; a frequency analyzing unit 42; a feature calculating unit 43; a classification unit 44; and a classification information setting unit 121. The classification information setting unit 121 performs a process of updating classification information in a case where information of a specimen of which the attribute of the tissue is found through a pathological examination or the like is added as known specimen information.

The storage unit 13 includes: a classification information storage unit 81; an attribute-determined image storage unit 131 that stores B-mode image data including a region to be examined whose attribute has been determined through a pathological examination or the like; and a known specimen information storage unit 132 that, for a known specimen, stores the value of the feature in association with the attribute of the tissue of the known specimen.

Figure 17:
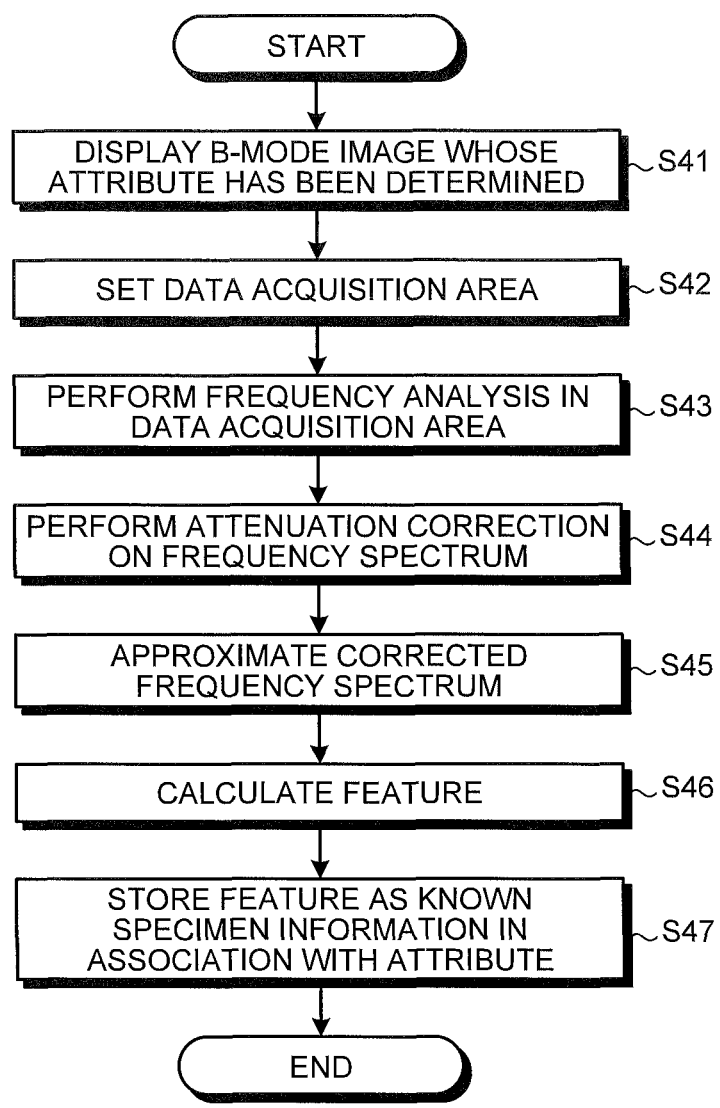
FIG. 17 is a flowchart that illustrates an overview of a process performed by the ultrasound observation apparatus according to the second embodiment of the present invention.

FIG. 17 is a flowchart that illustrates an overview of a known specimen information generating process performed by the ultrasound observation apparatus 11 having the configuration described above. Hereinafter, the known specimen information generating process will be described with reference to the flowchart illustrated in FIG. 17.

First, the control unit 9 reads, from the attribute-determined image storage unit 131, B-mode image data whose attribute has been determined and displays a B-mode image corresponding to this B-mode image data on the display unit 7 (Step S41).

Subsequently, the input unit 6, for the B-mode image that is in the middle of display, receives an input for setting a data acquisition area for generating known specimen information (Step S42). The data acquisition area, for example, is set as an area forming a shape such as a circle, an oval, a square, a rectangle, or a fan shape.

Thereafter, the frequency analyzing unit 42 performs a frequency analysis in the data acquisition area (Step S43). Subsequently, the attenuation correction unit 431 performs an attenuation correction on a frequency spectrum calculated by the frequency analyzing unit 42 (Step S44). Thereafter, the approximation unit 432 approximates the attenuation-corrected frequency spectrum by a linear expression by performing a regression analysis thereof at a predetermined frequency band (Step S45). The frequency analyzing process, the attenuation correction process, and the approximation process described here are performed similar to the frequency analyzing process, the attenuation correction process, and the approximation process described in the first embodiment.

After Step S45, the feature calculating unit 43 calculates features of a new population acquired by adding newly-calculated parameters to a group of known specimens configured by the same attribute (Step S46). For example, in a case where a slope a, an intercept b, and a mid-band fit c are calculated in the data acquisition area as parameters, a mean Mean S and a standard deviation Sd. S of the slopes a, a mean Mean I and a standard deviation Sd. I of the intercepts b, and a mean Mean M and a standard deviation Sd. M of the mid-band fit c of a population to which the calculated parameters are added are calculated as features.

Finally, the control unit 9 writes and stores the features calculated by the feature calculating unit 43 in the known specimen information storage unit 132 in association with the attributes (Step S47).

By performing the process of Steps S41 to S47 described above for a plurality of known specimens, information of the plurality of known specimens is accumulated in the known specimen information storage unit 132.

In the second embodiment, as an attribute, a new attribute can be added. For this reason, also in a case where a certain medical facility desires to define new attributes according to a criterion different from that of the other medical facilities or the like, information of known specimens can be accumulated according to the new attributes. In addition, also in a case where a disease name/tissue name or a category of disease/category of tissues is changed or newly added according to a revision of regulations such as a guideline for academic society or handling standards, information of known specimens can be accumulated based on the new attributes.

Figure 18:
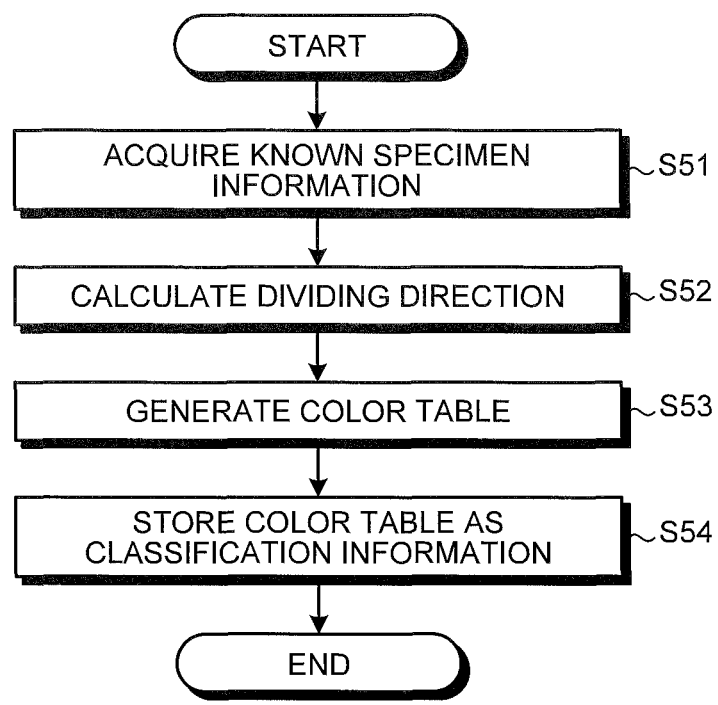
FIG. 18 is a flowchart that illustrates an overview of a process performed by a classification information setting unit of the ultrasound observation apparatus according to the second embodiment of the present invention.

FIG. 18 is a flowchart that illustrates an overview of a process performed by the classification information setting unit 121. Hereinafter, a classification information updating process performed by the classification information setting unit 121 in accordance with classification items will be described.

First, the classification information setting unit 121 acquires known specimen information by referring to the known specimen information storage unit 132 (Step S51). More specifically, the classification information setting unit 121 acquires information of features of each known specimen.

Subsequently, the classification information setting unit 121 calculates a direction for dividing the features of known specimens (Step S52). At this time, the classification information setting unit 121 performs calculation for setting a direction in which the attributes of determination targets are divided best when the grouping by the attributes of tissues of specimens is performed in a feature space, as a dividing direction.

Figure 19:
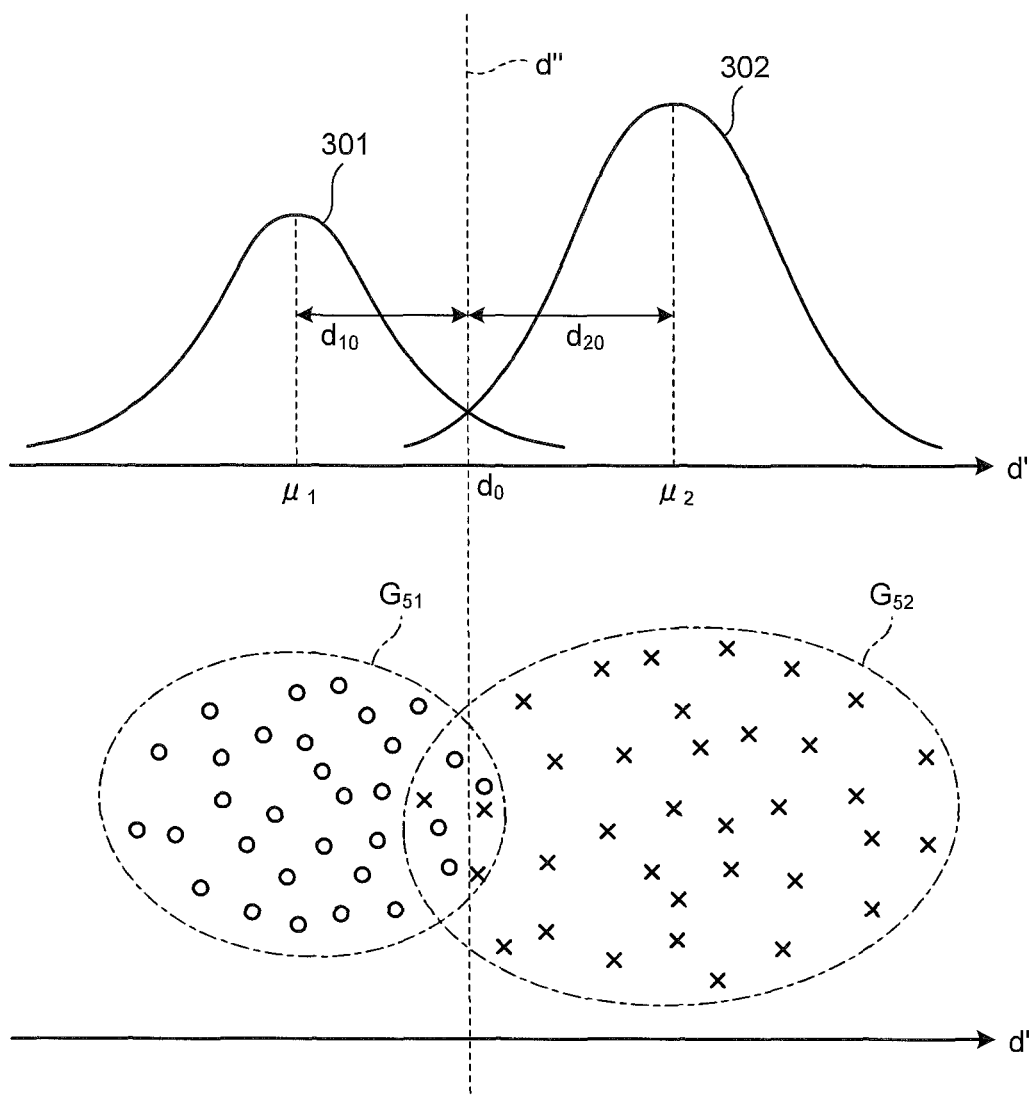
FIG. 19 is a diagram that schematically illustrates an overview of a process performed by the classification information setting unit of the ultrasound observation apparatus according to the second embodiment of the present invention.

FIG. 19 is a diagram that schematically illustrates an overview of the dividing direction determining process. FIG. 19 illustrates an example where the dividing direction of two groups $G_{51}$ and $G_{52}$ having different attributes is determined. A mean of a distribution 301 is denoted as $\mu_1$ when points (denoted by circular marks) in a feature space constituting the group $G_{51}$ are seen on an arbitrary axis d' in the feature space, and a standard deviation thereof is denoted as $\sigma_1$. Similarly, a mean of a distribution 302 is denoted as $\mu_2$ when points (denoted by x marks) in the feature space constituting the group $G_{52}$ are seen on the axis d', and a standard deviation thereof is denoted as $\sigma_2$. At this time, the classification information setting unit 121 calculates the direction of the axis d' in which the value of $(\mu_2-\mu_1)/\sigma'$ (here, $\sigma'=(\sigma_1+\sigma_2)/2$)) is a maximum as a direction for dividing the features of the known specimens. In addition, the classification information setting unit 121 sets, as a boundary between the group $G_{51}$ and the group $G_{52}$ in the direction d', a separation axis d" that is perpendicular to the direction d' and passes through a point $d_0$ internally dividing a line segment between $\mu_1$ and $\mu_2$ at the ratio of $\sigma_1:\sigma_2$. In the case illustrated in FIG. 19, a distance $d_{10}$ between $\mu_1$ and $d_0$ and a distance $d_{20}$ between $\mu_2$ and $d_0$ satisfy "$d_{10}:d_{20}=\sigma_1:\sigma_2$".

Thereafter, the classification information setting unit 121 generates a color table that associates each feature and the assignment of a color (Step S53). The classification information setting unit 121, for each area having a predetermined width along the dividing direction set in Step S52, determines a ratio between attributes of tissues of specimens included in each area and assigns a color corresponding to a result of the determination, thereby generating the color table.

More specifically, in the case illustrated in FIG. 19, the classification information setting unit 121, for example, divides each area along the axis d' for every width $\sigma_1/10$ and calculates a ratio between attributes of tissues of specimens in each area. Thereafter, the classification information setting unit 121 assigns a color that is different according to a ratio of the occupancy of points of the group $G_{51}$ in each area. For example, in a case where three divisional areas are formed according to the ratio of the occupancy of the points of the group $G_{51}$, different colors are assigned to an area in which the points of the group $G_{51}$ are included to be 70% or more of the total points, an area in which the points of the group $G_{51}$ are included to be 30% or more and less than 70% of the total points, and an area in which the points of the group $G_{51}$ are included to be less than 30% of the total points, whereby a color bar is generated. The number of divisional areas and colors to be assigned may be appropriately set. In addition, an area (mask area) to which any color is not assigned may be set.

Finally, the classification information setting unit 121, under the control of the control unit 9, writes and stores the generated color table into the classification information storage unit 81 as classification information (Step S54).

In the second embodiment, the feature image generating and displaying process performed by the ultrasound observation apparatus 11 is similar to that of the first embodiment.

According to the second embodiment of the present invention described above, similar to the first embodiment, the attributes of tissues of specimens can be classified based on an optical feature according to the content of the diagnosis, and image data in which tissues are classified according to the content of the diagnosis can be efficiently generated.

In addition, according to the second embodiment, effects similar to those of the first embodiment can be acquired in that a user can clearly identify the attribute of a tissue of a specimen, and the classification accuracy can be improved by performing an attenuation correction for an ultrasonic signal.

Furthermore, according to the second embodiment, features of regions to be examined in specimens of which the attributes of the tissues to be examined are found through a pathological examination or the like are accumulated as known specimen information, and the classification information can be updated, whereby classification having higher accuracy can be made.

Other Embodiments

Although the modes for carrying out the present invention has been described, the present invention is not limited to the embodiments described above. For example, the ultrasound observation apparatus 1, considering that the kinds of ultrasound probe 2 are different according to the use, may be configured to change selectable classification items in accordance with the kind of ultrasound probe 2. The correspondence between the kind of ultrasound probe 2 and selectable classification items may be stored in the classification information storage unit 81. In such a case, the kind of the ultrasound probe 2 included in the ultrasound observation apparatus 1 is configured to be recognized by the apparatus in advance. More specifically, for example, in a case where an ultrasound endoscope is used as the ultrasound probe 2, a connection pin used for allowing a processing device to determine the kind of ultrasound endoscope may be arranged in an end portion of the ultrasound endoscope that is disposed on the processing device connection side. In such a case, the processing device can determine the kind of ultrasound endoscope based on the shape of the connection pin of the connected ultrasound endoscope.

In the first embodiment of the present invention, the information of colors for features (for example, the value of Mean M) and the color table associating the domain of the feature and the visual information with each other are calculated based on the distribution of known specimens. Then, the classification information storage unit 81 included in the storage unit 8 stores the information of the color and the color table as a part of the classification information. However, the present invention is not limited to the embodiment but may be configured as below. For example, the classification information storage unit 81 may store, in advance, received signals, digital RF signals obtained by performing A/D conversion on the received signals by the transmitting and receiving unit 3, or the frequency spectra of all the known specimens that are necessary for constituting the distributions illustrated in FIGS. 8 to 11. In such a case, before Step S2 in which the measurement of a new specimen of which the attribute is unknown is performed, the feature calculating unit 43 calculates features of all the known specimens based on the above-described information of all the known specimens in advance, the classification unit 44 calculates a part (in other words, the information of colors and the color table described above) of the classification information based on such features, and the classification information storage unit 81 stores this classification information again. In this way, information calculated based on the received signal from a specimen of which the attribute is known or the received signal may be used as the "known specimen information". With this configuration, effects similar to those of the first embodiment of the present invention can be acquired. In addition, it is apparent that such a configuration may be applied to the second embodiment of the present invention.

In addition, for the ultrasound probe 2 designed for specific use, classification items may be limited according to the specific use. Examples of the ultrasound probe 2 designed for specific use include a miniature probe having a small diameter. The miniature probe is configured to be inserted into not only an alimentary tract or a blood vessel but also, particularly, a bile duct, a pancreatic duct, or the like and is used for performing the classification item "Malignancy/Benignancy Distinction" included in the table Tb illustrated in FIG. 7. For this reason, the ultrasound observation apparatus 1 to which the miniature probe is connected may be configured to automatically perform a classification process for the classification item "Malignancy/Benignancy Distinction".

Figure 20:
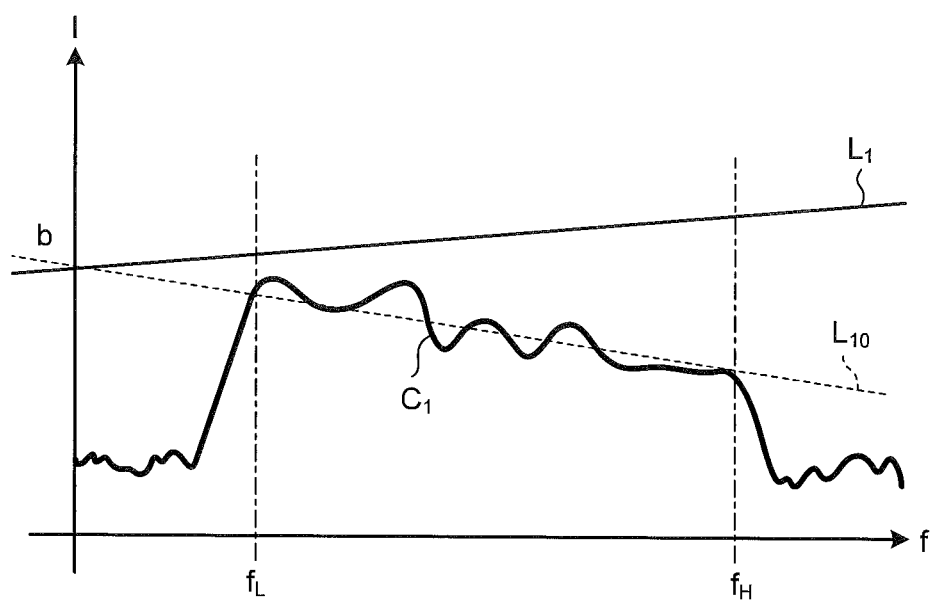
FIG. 20 is a diagram that schematically illustrates an overview of a process performed by a feature calculating unit of the ultrasound observation apparatus according to another embodiment of the present invention.

In addition, as the features, the slope, the intercept, and the mid-band fit that are parameters acquired by approximating the frequency spectrum before the attenuation correction may be used. Furthermore, such features may be calculated by performing approximation before an attenuation correction of the frequency spectrum and performing an attenuation correction for a result of the approximation. FIG. 20 is a diagram that schematically illustrates an overview of a process performed in a case where the feature calculating unit 43 performs an approximation process of the frequency spectrum and then performs the attenuation correction process. A straight line $L_{10}$ illustrated in FIG. 20 is a regression line acquired as a result of the approximation of the frequency band F of the frequency spectrum $C_1$ that is performed by the approximation unit 432. The attenuation correction unit 431 performs an attenuation correction on the straight line $L_{10}$ to acquire a straight line $L_1$. The feature calculating unit 43 calculates the slope, the intercept, and the mid-band fit of this straight line $L_1$ as features.

In addition, as a feature other than the features calculated through a frequency analysis, for example, a texture feature may be applied. Examples of such a texture feature include energy, entropy, a correlation, local homogeneity, inertia, a short run emphasis, a long run emphasis, a gray level distribution, a run length distribution, a run percentage, or the like of the luminance within a region of interest (for more detail, see JP 4-236952 A, for example). In addition, the attributes of tissues may be classified by appropriately combining such a texture feature and the features acquired through the frequency analysis. Furthermore, the pattern of the color or the luminance superimposed on a feature image may be analyzed, a texture feature may be calculated based on the pattern, and the classification may be made based thereon.

Instead of employing colors as the visual information and using a color table, it may be configured such that the luminance is employed as the visual information, a luminance table displaying a difference in the attribute in accordance with a difference in the luminance is generated, and feature image data is generated using the luminance table.

In addition, a user such as a medical doctor may be allowed to change the classification item in the middle of an examination. In such a case, in a case where an input of a classification item switching signal is received by the input unit 6, the control unit 9 may cause the display unit 7 to display the selection screen 101 illustrated in FIG. 13. With such a configuration and operation, after a lesion such as a tumor is found by the user in the classification item "I. Tumor Screening", during the examination, the user can determine whether the lesion is malignant or benign and whether a follow-up or an immediate treatment is required by switching between the classification item "II Malignancy/Benignancy Distinction", the classification item "III. Follow-up Determination 1", and the classification item "IV. Follow-up Determination 2" with a simple operation. Accordingly, a re-examination for a further evaluation after the screening is not required, and the medical treatment can be performed very efficiently.

With reference to FIGS. 8 to 10, the classification based on one kind of feature has been described. This means that the classification can be made also in a case where the feature space takes one dimension. In addition, in FIG. 11, the classification using two kinds of features has been described. This means that the classification can be made by taking the feature space in two dimensions. However, the kinds of features used for the classification, in other words, the dimension of the feature space is not limited to such examples but may be three or higher dimensions. In a case where the feature space has a high dimension, the separation axis d" illustrated in FIG. 19 becomes a partial space within a feature space of not one dimension but two (plane) or more dimensions.

In the first and second embodiments, while the mean and the standard deviation have been described as statistics that are features as an example, as described above, the dispersion may be used. In addition, the statistics are not limited to statistics of one dimension. In a case where the feature space has two dimensions as illustrated in FIG. 11, statistics of multiple dimensions such as a correlation coefficient, principal axis of inertia, tensor of inertia, an eigenvalue, and an eigenvector may be calculated for the groups $G_{41}$ and $G_{42}$ and used as a feature. In a case where the feature space has three or more dimensions, material points having different masses are considered to be distributed in a two or higher dimensional space. Accordingly, a statistic such as a sum of squares (energy) calculated by regarding the center of the distribution, the moment of mass, or the mass as the amplitude may be calculated and used as a feature.

A medical diagnostic apparatus according to some embodiments may be realized as a general endoscope, an X-ray computed tomography (CT), magnetic resonance imaging (MRI), or an extra corporeal ultrasound diagnostic apparatus that emitting an ultrasound wave from a body surface such as a chest or an abdomen.

According to some embodiments, a plurality of kinds of features are calculated based on a received signal from a specimen, attributes of a tissue of the specimen are classified by using a feature determined according to a classification item selected in advance among the plurality of kinds of features, and feature image data in which visual information according to a classification result is assigned to pixels of an image based on the received signal is generated. Accordingly, it is possible to classify the attributes of the tissue of the specimen based on an optimal feature according to a content of diagnosis, and to efficiently generate image data in which tissues are classified according to the content of the diagnosis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical diagnostic apparatus comprising:
    a processor comprising hardware, wherein the processor is configured to:
        perform a frequency analyzing process comprising analyzing a frequency of a received signal from a specimen to calculate a frequency spectrum;
        perform a feature calculating process comprising calculating a plurality of kinds of features that is based on frequency spectrum information obtained from the received signal from the specimen, the plurality of kinds of features relating to attributes of a tissue of the specimen, the attributes of the tissue comprising at least two of a malignant tumor tissue, a benign tumor tissue, an endocrine tumor tissue, a mucinous tumor tissue, a normal tissue, and a vessel;
        perform a classification process comprising:
            classifying the attributes of the tissue of the specimen by using a feature determined among the plurality of kinds of features calculated in the feature calculating process according to a classification item selected in advance from a plurality of classification items assigned for each classification purpose, the plurality of classification items comprising at least two of tumor screening, distinction between malignancy and benignancy, and follow-up determination; and
            assigning visual information according to a classification result to pixels of an image based on the received signal; and
        perform a feature image data generating process comprising generating feature image data on which the visual information assigned to the pixels of the image based on the received signal is superimposed,
    wherein the feature calculating process comprises an approximation process comprising:
        approximating, by a linear expression, the frequency spectrum calculated by the frequency analyzing process; and
        extracting, as the plurality of kinds of features, at least one of a slope of the linear expression an intercept of the linear expression, and an intensity defined by using the slope, the intercept, and a specific frequency in a frequency band of the frequency spectrum.

2. The medical diagnostic apparatus according to claim 1, further comprising a classification information storage configured to store classification information including at least one of an attribute of a tissue to be classified corresponding to the classification item, a kind of a feature used for classification, and information associating visual information according to a value of the feature,
    wherein the classification process comprises performing classification and assignment of the visual information by referring to the classification information storage.

3. The medical diagnostic apparatus according to claim 2, further comprising:
    a known specimen information storage configured to store known specimen information including at least one of a received signal from a specimen whose attribute is known and information calculated based on the received signal such that the known specimen information is associated with the attribute,
    wherein the processor is configured to perform a classification information setting process comprising setting the classification information by using the known specimen information stored in the known specimen information storage.

4. The medical diagnostic apparatus according to claim 1, wherein the feature calculating process comprises:
    extracting a plurality of parameters based on the received signal from a predetermined area of the specimen; and
    calculating the features by using the plurality of parameters.

5. The medical diagnostic apparatus according to claim 4, wherein the feature calculating process comprises calculating, as the features, a statistic of parameters of same type among the plurality of parameters.

6. The medical diagnostic apparatus according to claim 1, wherein the visual information is a variable constituting a color space.

7. The medical diagnostic apparatus according to claim 1, wherein the visual information is luminance.

8. The medical diagnostic apparatus according to claim 1, further comprising a display configured to display a feature image corresponding to the feature image data generated by the feature image data generating process.

9. The medical diagnostic apparatus according to claim 1, further comprising an input device configured to receive an input for selecting the classification item.

10. The medical diagnostic apparatus according to claim 1, further comprising an ultrasound probe configured to transmit an ultrasound wave to the specimen and to receive, as the received signal, an electric echo signal acquired by converting an ultrasound echo reflected from the specimen.

11. The medical diagnostic apparatus according to claim 10,
    wherein the frequency analyzing process comprises analyzing the frequency of the echo signal to calculate the frequency spectrum, and wherein the feature calculating process comprises calculating the plurality of kinds of features by using the frequency spectrum.

12. The medical diagnostic apparatus according to claim 1,
wherein the feature calculating process comprises calculating, as the plurality of kinds of features, texture features obtained by a texture analysis from luminance of each of the pixels of the image based on the received signal.

13. A method for operating a medical diagnostic apparatus that generates diagnostic image data based on a received signal from a specimen, the method comprising:
analyzing, by a frequency analyzing process, a frequency of the received signal from the specimen to calculate a frequency spectrum;
calculating, by a feature calculating process, a plurality of kinds of features in frequency spectrum information obtained from the received signal;
by a classification process, classifying attributes of a tissue of the specimen by using a feature determined among the plurality of kinds of features according to a classification item selected in advance from a plurality of classification items assigned for each classification purpose, and assigning visual information according to a classification result to pixels of an image based on the received signal, the attributes of the tissue comprising at least two of a malignant tumor tissue, a benign tumor tissue, an endocrine tumor tissue, a mucinous tumor tissue, a normal tissue, and a vessel, and the plurality of classification items comprising at least two of tumor screening, distinction between malignancy and benignancy, and follow-up determination; and
generating, by a feature image data generating process, feature image data on which the visual information assigned to the pixels of the image based on the received signal is superimposed,
wherein calculating the plurality of kinds of features comprises:
approximating, by a linear expression, the frequency spectrum calculated by the frequency analyzing process; and
extracting, as the plurality of kinds of features, at least one of a slope of the linear expression, an intercept of the linear expression, and an intensity defined by using the slope, the intercept, and a specific frequency in a frequency band of the frequency spectrum.

14. A non-transitory computer-readable recording medium with an executable program stored thereon, the program instructing a medical diagnostic apparatus that generates diagnostic image data based on a received signal from a specimen, to execute:
analyzing, by a frequency analyzing process, a frequency of the received signal from the specimen to calculate a frequency spectrum;
calculating, by a feature calculating process, a plurality of kinds of features in frequency spectrum information obtained from the received signal;
by a classification process, classifying attributes of a tissue of the specimen by using a feature determined among the plurality of kinds of features according to a classification item selected in advance from a plurality of classification items assigned for each classification purpose, and assigning visual information according to a classification result to pixels of an image based on the received signal, the attributes of the tissue comprising at least two of a malignant tumor tissue, a benign tumor tissue, an endocrine tumor tissue, a mucinous tumor tissue, a normal tissue, and a vessel, and the plurality of classification items comprising at least two of tumor screening, distinction between malignancy and benignancy, and follow-up determination; and
generating, by a feature image data generating process, feature image data on which the visual information assigned to the pixels of the image based on the received signal is superimposed,
wherein calculating the plurality of kinds of features comprises:
approximating, by the linear expression, the frequency spectrum calculated by the frequency analyzing process; and
extracting, as the plurality of kinds of features, at least one of a slope of the linear expression, an intercept of the linear expression, and an intensity defined by using the slope, the intercept, and a specific frequency in a frequency band of the frequency spectrum.

* * * * *